United States Patent
Hooven

(10) Patent No.: US 9,204,922 B2
(45) Date of Patent: Dec. 8, 2015

(54) METHOD AND APPARATUS FOR REMODELING/PROFILING A TISSUE LUMEN, PARTICULARLY IN THE URETHRAL LUMEN IN THE PROSTATE GLAND

(75) Inventor: Michael D. Hooven, Cincinnati, OH (US)

(73) Assignee: Enable Urology, LLC, Cincinnati, OH (US)

( * ) Notice: Subject to any disclaimer, the term of this patent is extended or adjusted under 35 U.S.C. 154(b) by 74 days.

(21) Appl. No.: 13/991,023

(22) PCT Filed: Nov. 30, 2011

(86) PCT No.: PCT/US2011/062586
§ 371 (c)(1),
(2), (4) Date: May 31, 2013

(87) PCT Pub. No.: WO2012/075112
PCT Pub. Date: Jun. 7, 2012

(65) Prior Publication Data
US 2013/0253622 A1    Sep. 26, 2013

Related U.S. Application Data

(60) Provisional application No. 61/418,476, filed on Dec. 1, 2010.

(51) Int. Cl.
*A61B 18/14*    (2006.01)
*A61B 17/00*    (2006.01)
(Continued)

(52) U.S. Cl.
CPC ............. *A61B 18/14* (2013.01); *A61B 18/1492* (2013.01); *A61B 2017/00026* (2013.01);
(Continued)

(58) Field of Classification Search
CPC ........... A61B 18/1402; A61B 18/1492; A61B 2018/0016; A61B 2018/00517; A61B 2018/00267; A61B 2018/00547; A61B 2018/00285; A61B 2017/00274; A61M 2210/166
USPC .......................... 606/48, 47; 607/99, 126, 143
See application file for complete search history.

(56) References Cited

U.S. PATENT DOCUMENTS

| 4,311,154 A | 1/1982 | Sterzer et al. |
| 5,007,437 A | 4/1991 | Sterzer |

(Continued)

FOREIGN PATENT DOCUMENTS

| WO | WO 00/10472 A1 | 3/2000 |
| WO | WO 01/80723 A2 | 11/2001 |

(Continued)

OTHER PUBLICATIONS

Fred Sterzer, Ph.D., MMTC, Inc., Princeton, NJ, "Localized Heating of Deep-Seated Tissues Using Microwave Balloon Catheters", New Frontiers in Medical Device Technology, Edited by Arye Rosen & Hare! Rosen, ISBN 0-471-59189-0, Copyright 1995 by John Wiley & Sons, Inc., Chapter 4: pp. 105-120.

(Continued)

*Primary Examiner* — Michael Peffley
*Assistant Examiner* — Thomas Giuliani
(74) *Attorney, Agent, or Firm* — Cook Alex Ltd.

(57) ABSTRACT

Apparatus for tissue lumen (such as urethra) remodeling includes an elongated shaft and at least one expandable structure on a distal end of the shaft. At least one desiccator or energy emitter is carried by the structure and operable to define a support structure in lumen tissue that resists lumen closure. Apparatus is also disclosed for identifying tissue or developing a profile of tissue along the lumen based at least in part on an electrical characteristic of the tissue. Methods of remodeling and profiling are also disclosed.

17 Claims, 25 Drawing Sheets

(51) Int. Cl.
A61B 18/00 (2006.01)
A61M 25/04 (2006.01)
A61N 1/40 (2006.01)

(52) U.S. Cl.
CPC .......... A61B2017/00199 (2013.01); A61B 2017/00274 (2013.01); A61B 2018/0016 (2013.01); A61B 2018/00232 (2013.01); A61B 2018/00267 (2013.01); A61B 2018/00285 (2013.01); A61B 2018/00517 (2013.01); A61B 2018/00547 (2013.01); A61B 2018/00827 (2013.01); A61B 2018/00875 (2013.01); A61B 2018/00892 (2013.01); A61B 2018/1435 (2013.01); A61M 25/04 (2013.01); A61M 2205/3317 (2013.01); A61M 2210/166 (2013.01); A61N 1/403 (2013.01)

(56) References Cited

U.S. PATENT DOCUMENTS

| | | | |
|---|---|---|---|
| 5,234,004 | A | 8/1993 | Hascoet et al. |
| 5,330,518 | A | 7/1994 | Neilson et al. |
| 5,386,837 | A | 2/1995 | Sterzer |
| 5,480,417 | A | 1/1996 | Hascoet et al. |
| 5,509,929 | A | 4/1996 | Hascoet et al. |
| 5,688,050 | A | 11/1997 | Sterzer et al. |
| 5,949,845 | A | 9/1999 | Sterzer |
| 5,992,419 | A * | 11/1999 | Sterzer et al. .......... 128/898 |
| 6,081,749 | A | 6/2000 | Ingle et al. |
| 6,122,551 | A | 9/2000 | Rudie et al. |
| 6,216,704 | B1 | 4/2001 | Ingle et al. |
| 6,272,384 | B1 | 8/2001 | Simon et al. |
| 6,470,217 | B1 | 10/2002 | Fenn et al. |
| 6,477,426 | B1 | 11/2002 | Fenn et al. |
| 6,496,737 | B2 | 12/2002 | Rudie et al. |
| 6,638,275 | B1 | 10/2003 | McGaffigan et al. |
| 6,690,976 | B2 | 2/2004 | Fenn et al. |
| 6,725,095 | B2 | 4/2004 | Fenn et al. |
| 6,768,925 | B2 | 7/2004 | Fenn et al. |
| 6,788,977 | B2 | 9/2004 | Fenn et al. |
| 6,807,446 | B2 | 10/2004 | Fenn et al. |
| 6,847,848 | B2 | 1/2005 | Sterzer et al. |
| 6,958,075 | B2 | 10/2005 | Mon et al. |
| 2006/0100506 | A1 * | 5/2006 | Halperin et al. .......... 600/424 |
| 2008/0125772 | A1 * | 5/2008 | Stone et al. .......... 606/41 |

FOREIGN PATENT DOCUMENTS

| | | | |
|---|---|---|---|
| WO | WO 2007014063 A2 | 2/2007 | |
| WO | WO 2009/036468 A1 | 3/2009 | |
| WO | WO 2009/036468 A1 * | 3/2009 | .......... A61B 18/14 |
| WO | WO 2012/075112 A1 | 6/2012 | |

OTHER PUBLICATIONS

Arye Rosen, Arnold J. Greenspon and Paul Walinsky, "Microwaves Treat Heart Disease", IEEE Microwave Magazine, Feb. 2007: pp. 70-75.

National Kidney and Urologic Diseases Information Clearing (NKUDIC), "Prostate Englargement: Benign Prostatic Hyperplasia", NIH Publication No. 07-3012, Jun. 2006, (12 pages), From: http://www.kidney.niddk.nih.gov/kudiseases/pubs/prostateenlargement/.

Freedom of Information Response, May 17, 2010, National Institute of Health re Grant No. 2R44CA086656, 57 pages.

"Biological Stents for Treating BPH", Grant No. IR43DK051426-01 (1996—noabstract available), National Institute of Diabetes and Digestive and Kidney Diseases IRG: ZRG7, 1 pg.

Abstract, "Self-Calibrating Diagnostic Digital Radiometer", Grant No. 1 R43RR018024-01 (2003), National Center for Research Resources IRG: ZRG1, 1 pg.

Abstract, "Self-Calibrating Diagnostic Digital Radiometer", Grant No. 5R44RR018024-03 (1999), National Center for Research Resources IRG: ZRG1, 1 pg.

Abstract, "Biological Stents for Treating BPH", Grant No. 2R44DK051426-02A1 (1999), National Institute of Diabetes and Digestive and Kidney Diseases IRG: ZRG7, 1 pg.

Abstract, "Microwave Treatment of Localized Prostate Cancer", Grant No. 1 R43CA086656-01 (2000), National Center Cancer Institute IRG: ZRG1, 1 pg.

Notification of Transmittal of the International Search Report, International Search Report and Written Opinion for PCT /US2011/062586 dated Feb. 27, 2012.

* cited by examiner

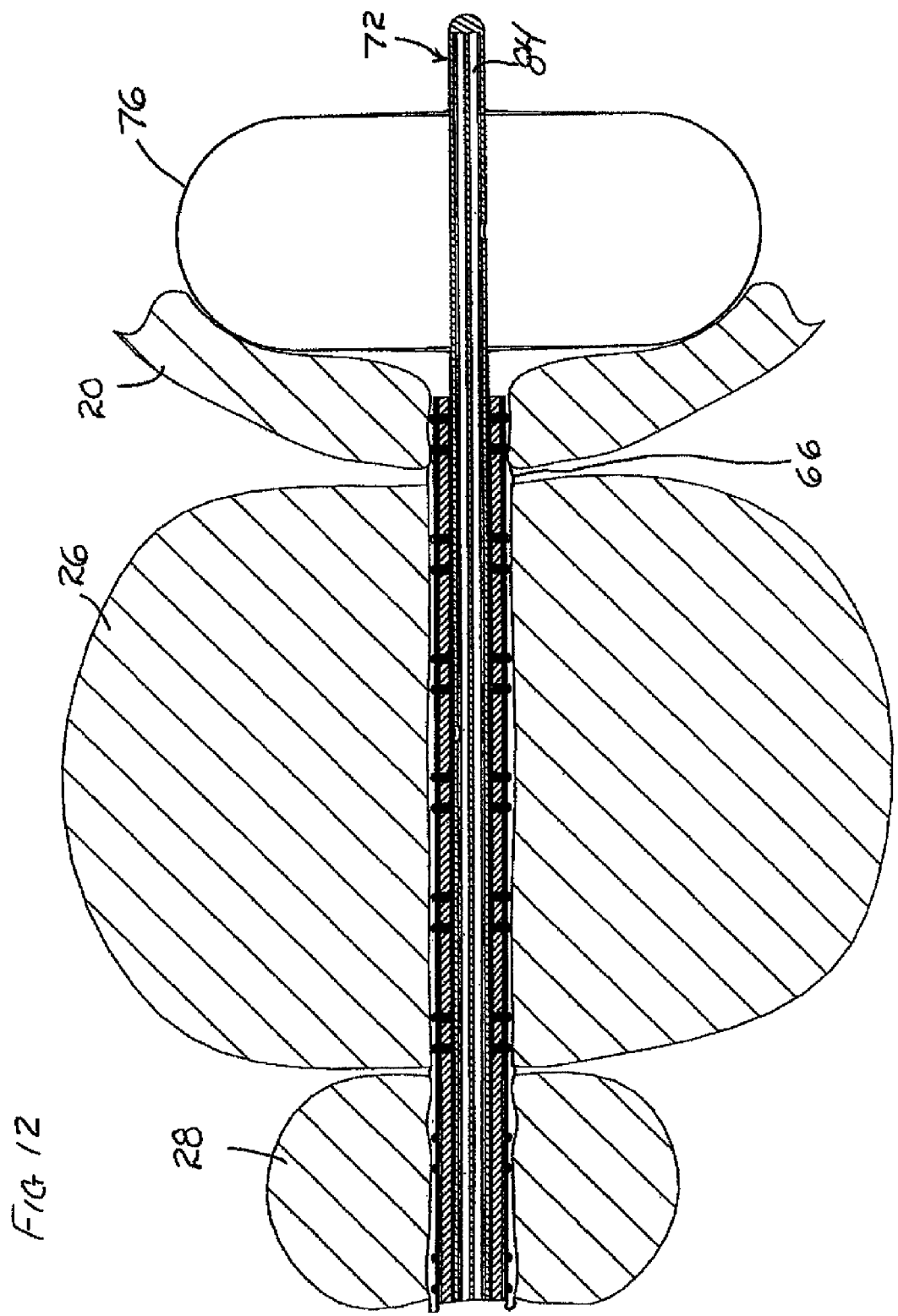

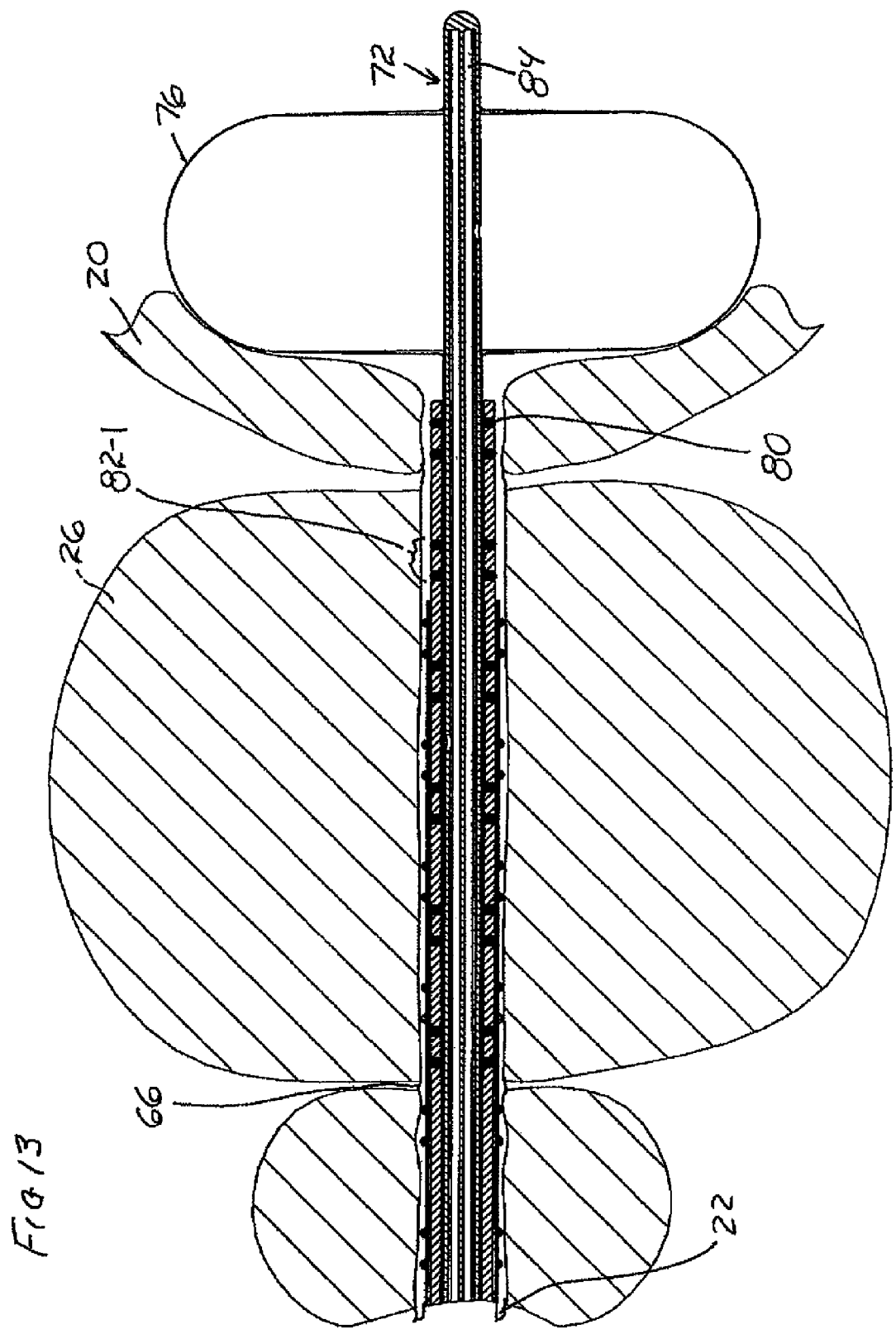

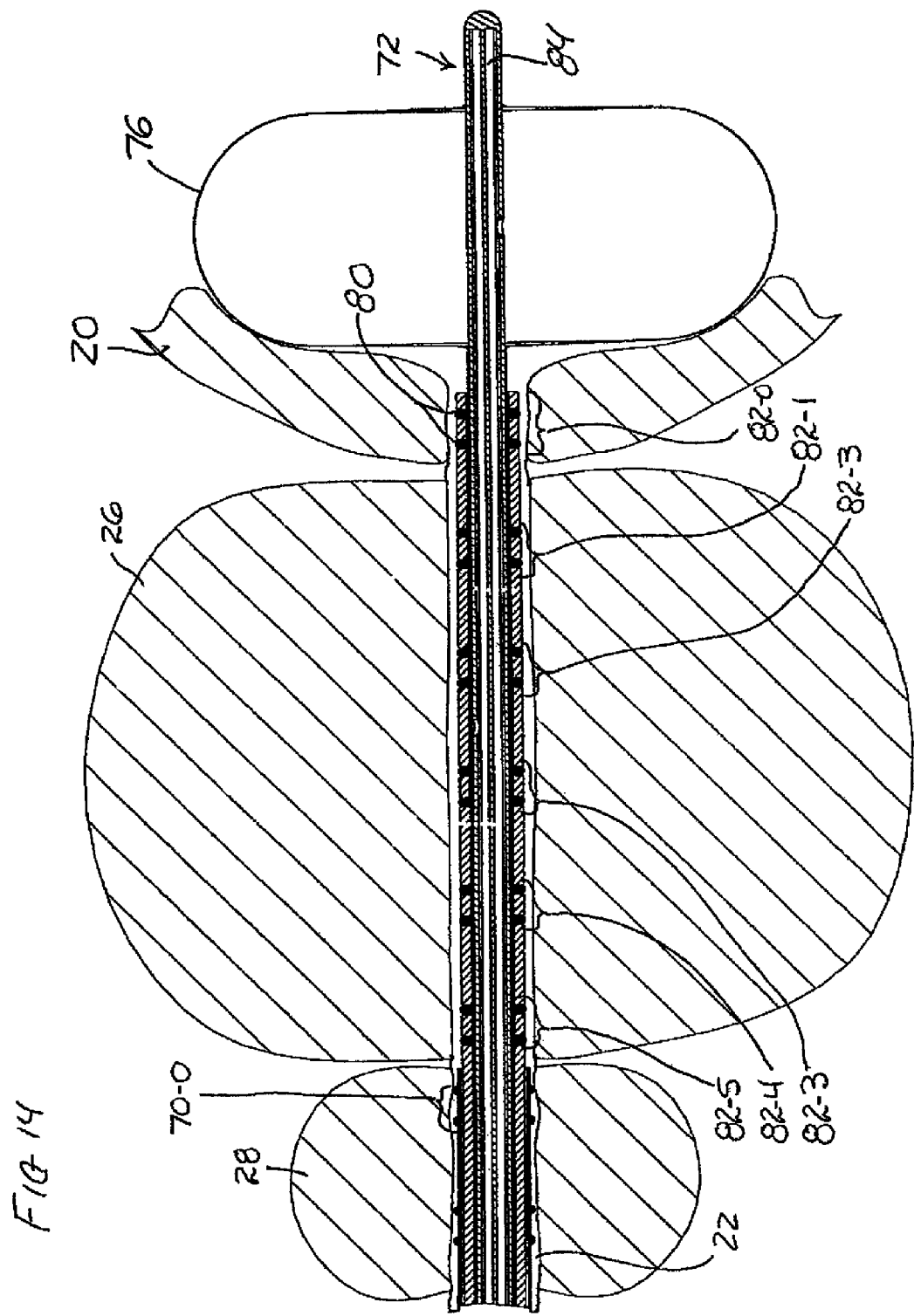

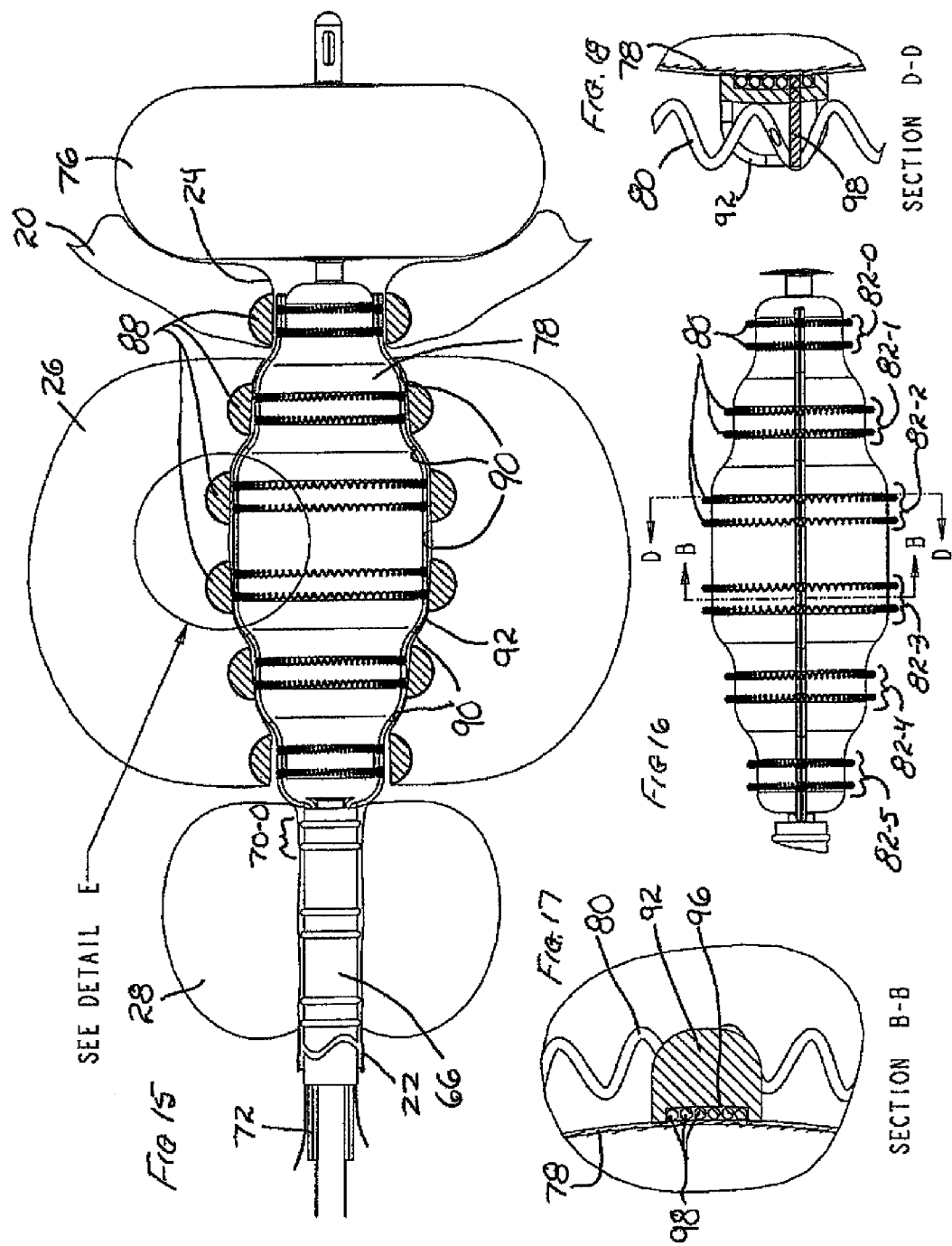

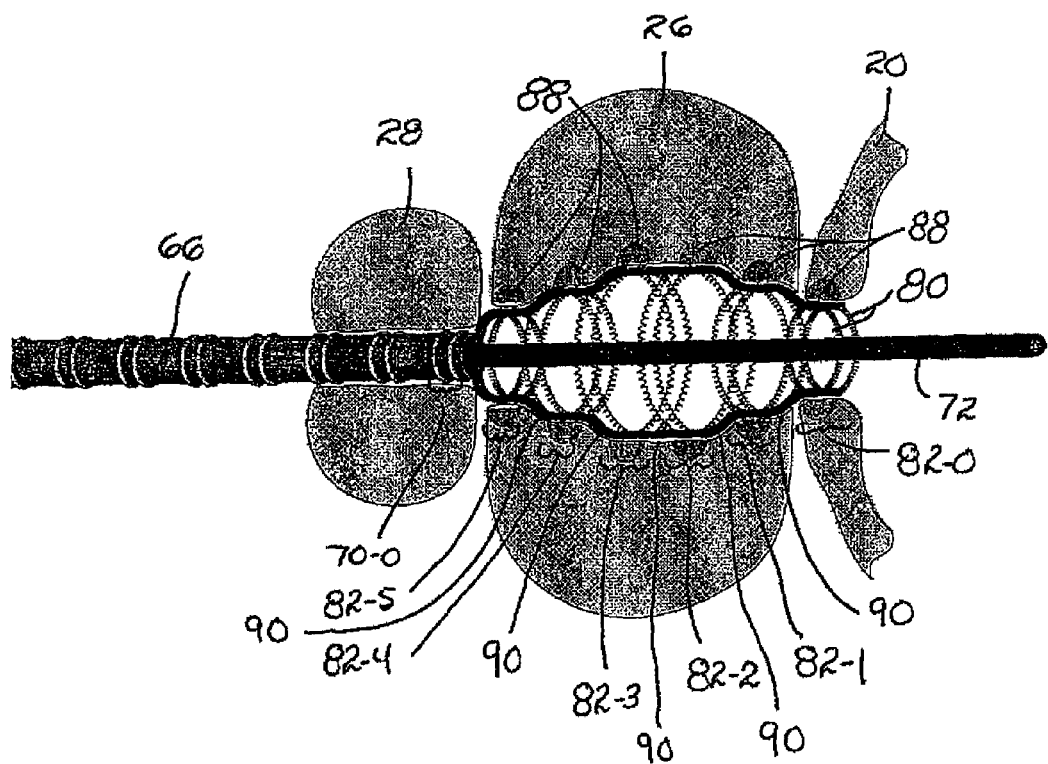

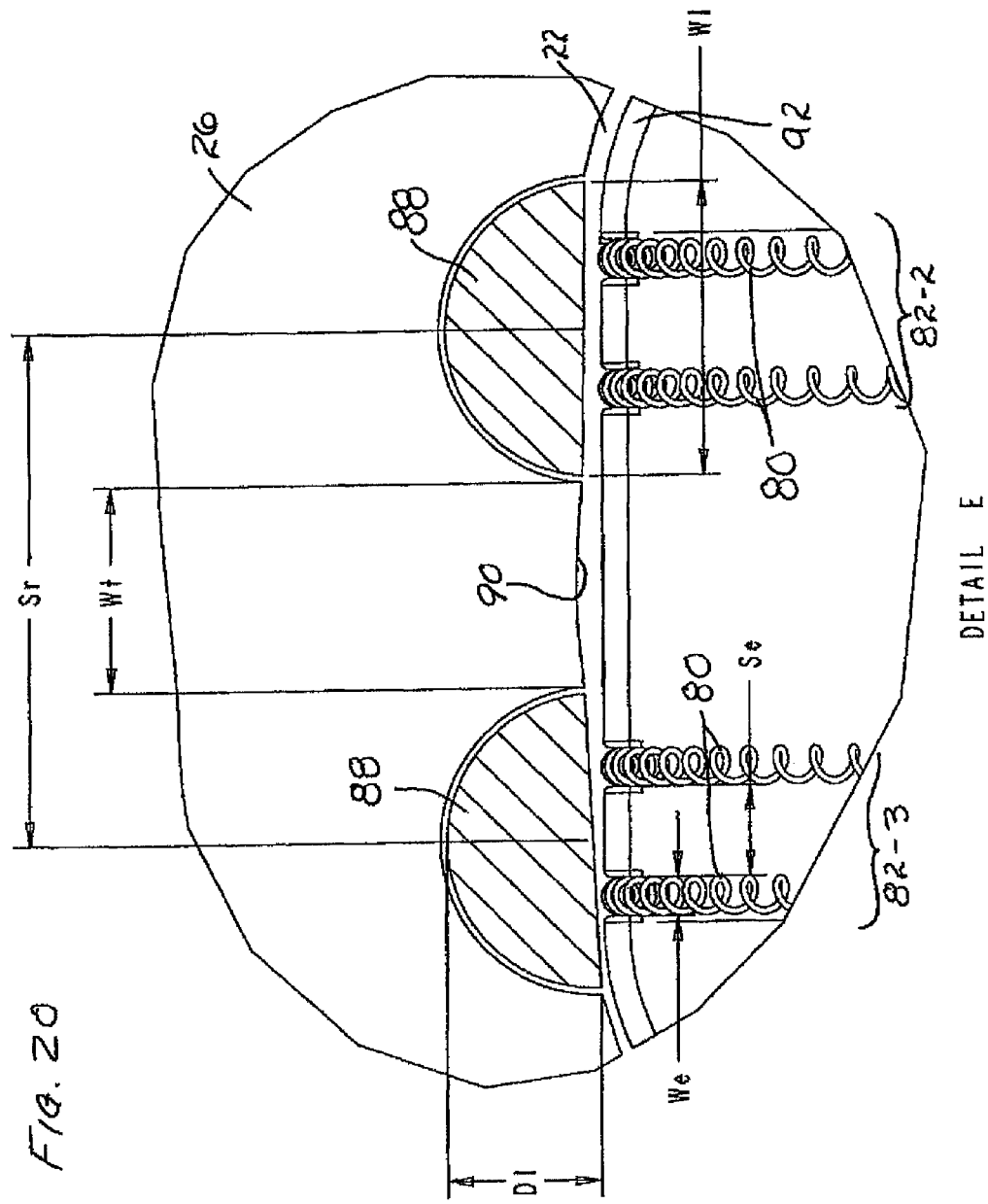

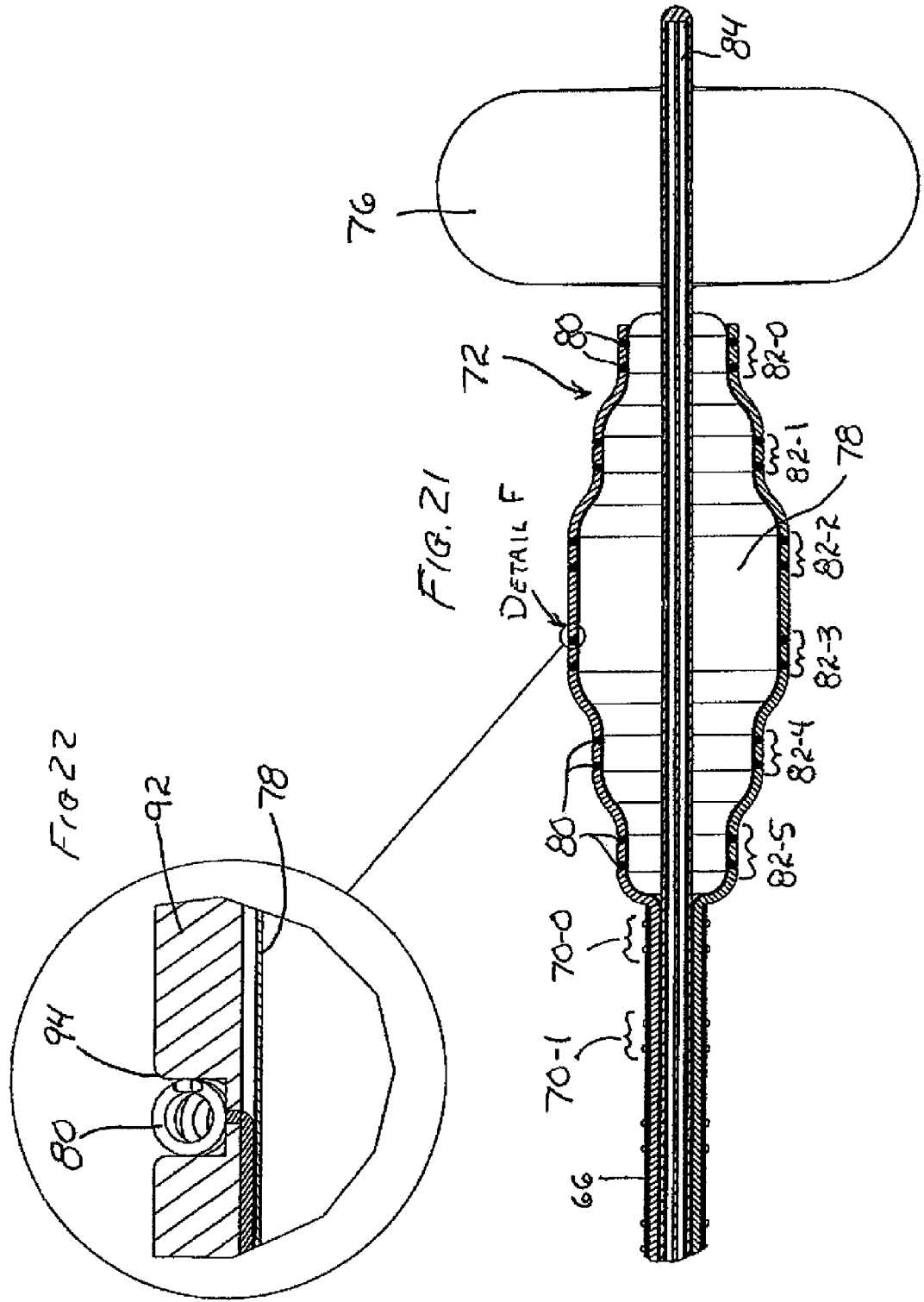

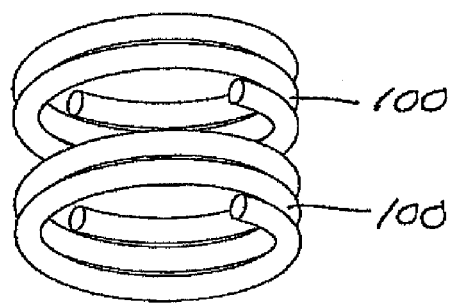
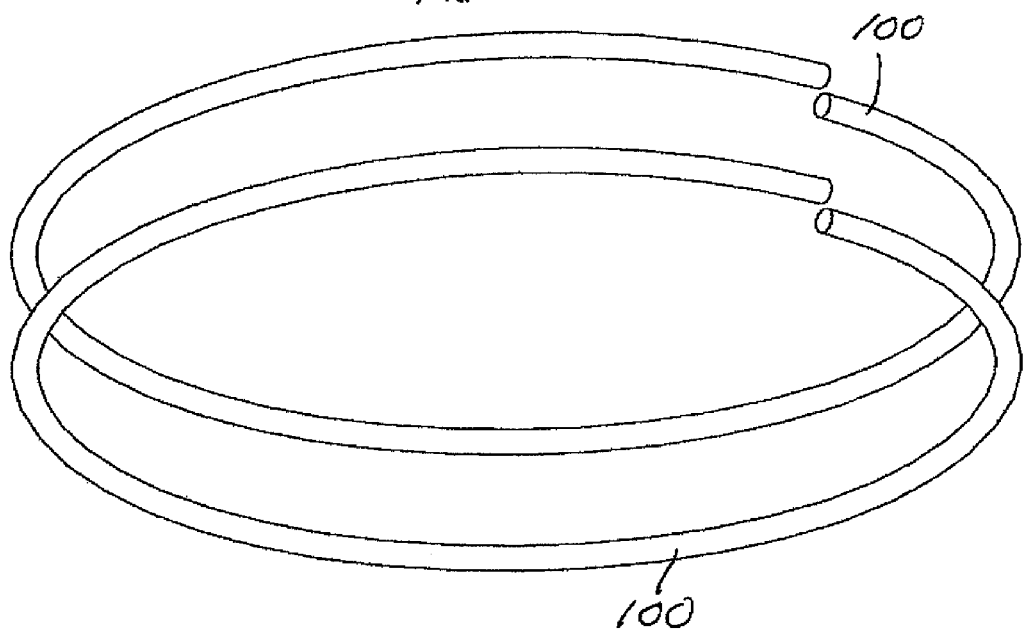

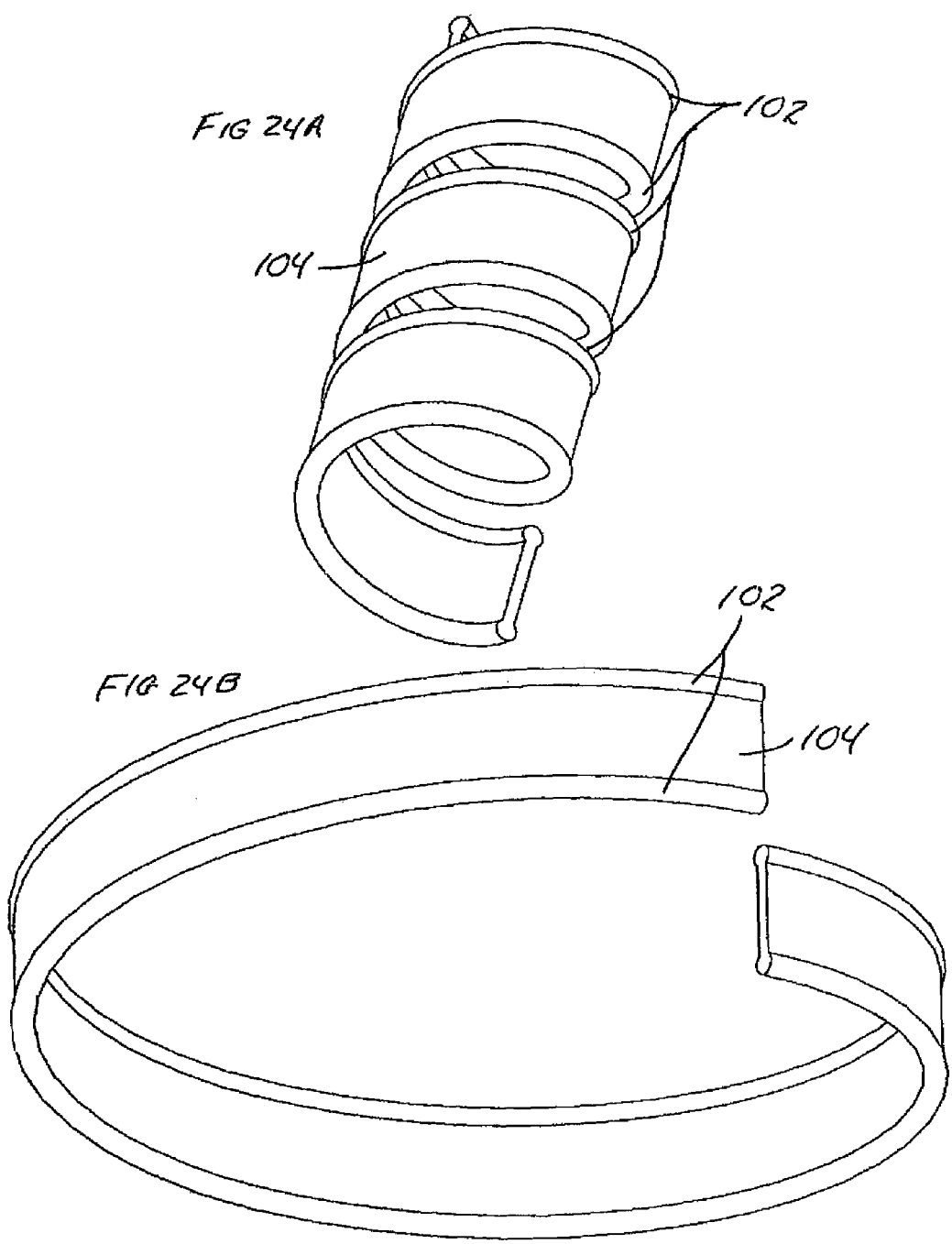

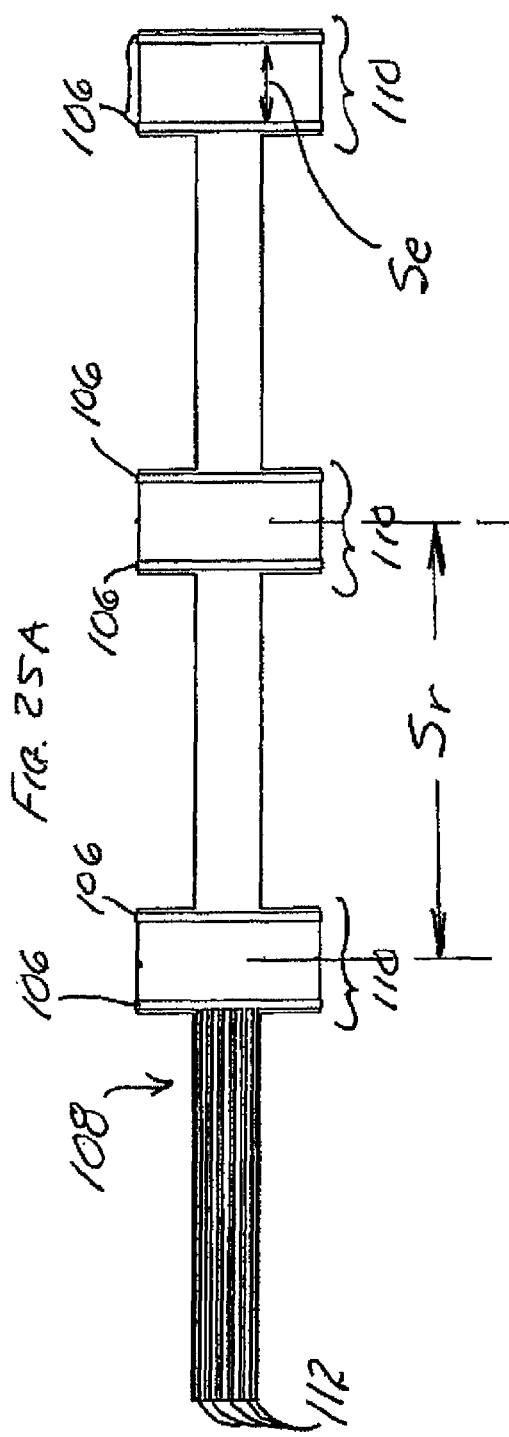
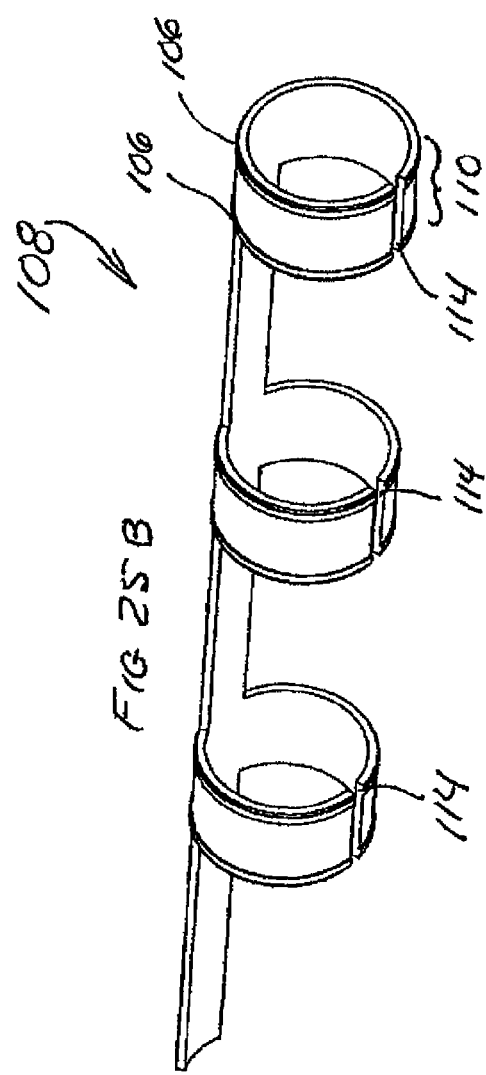

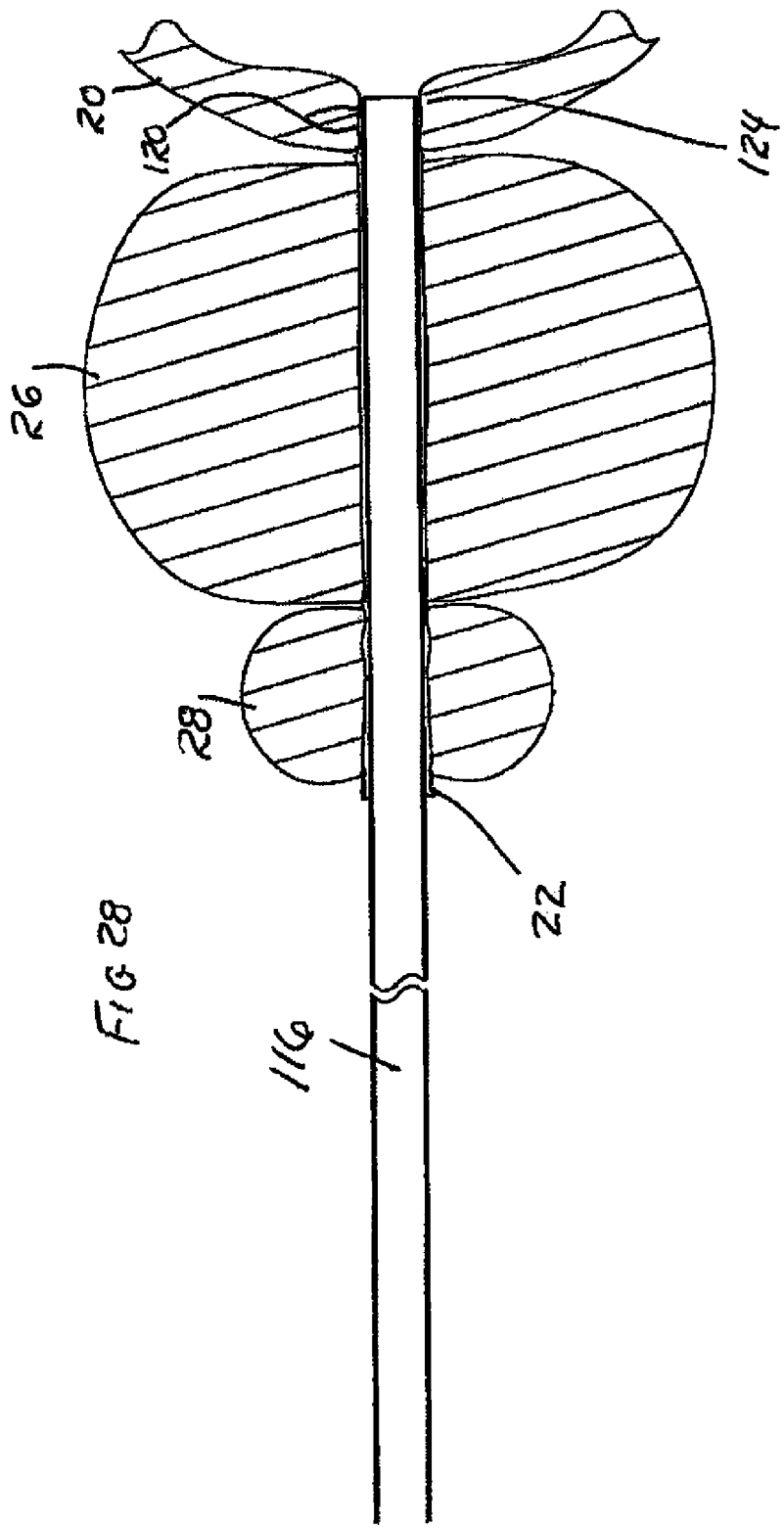

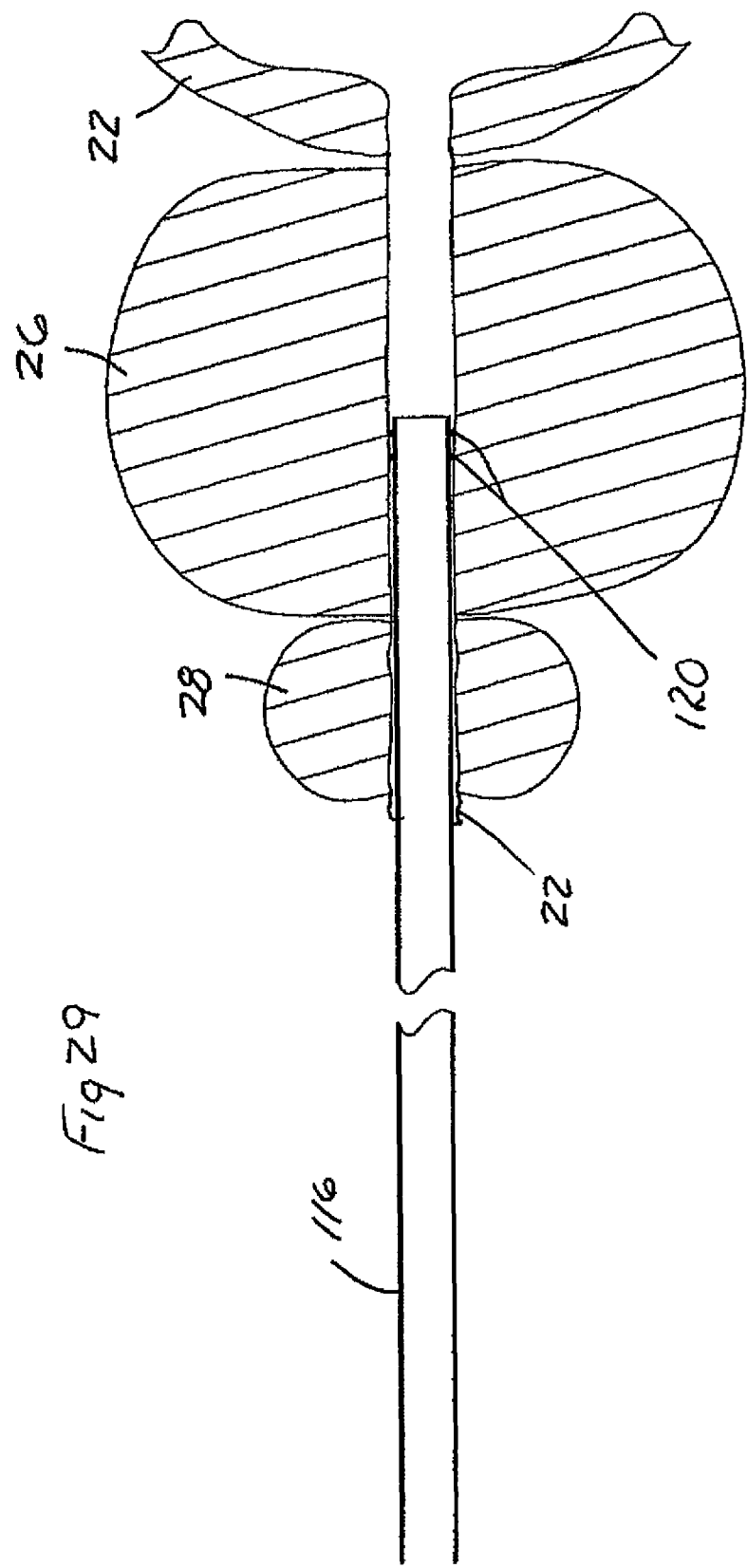

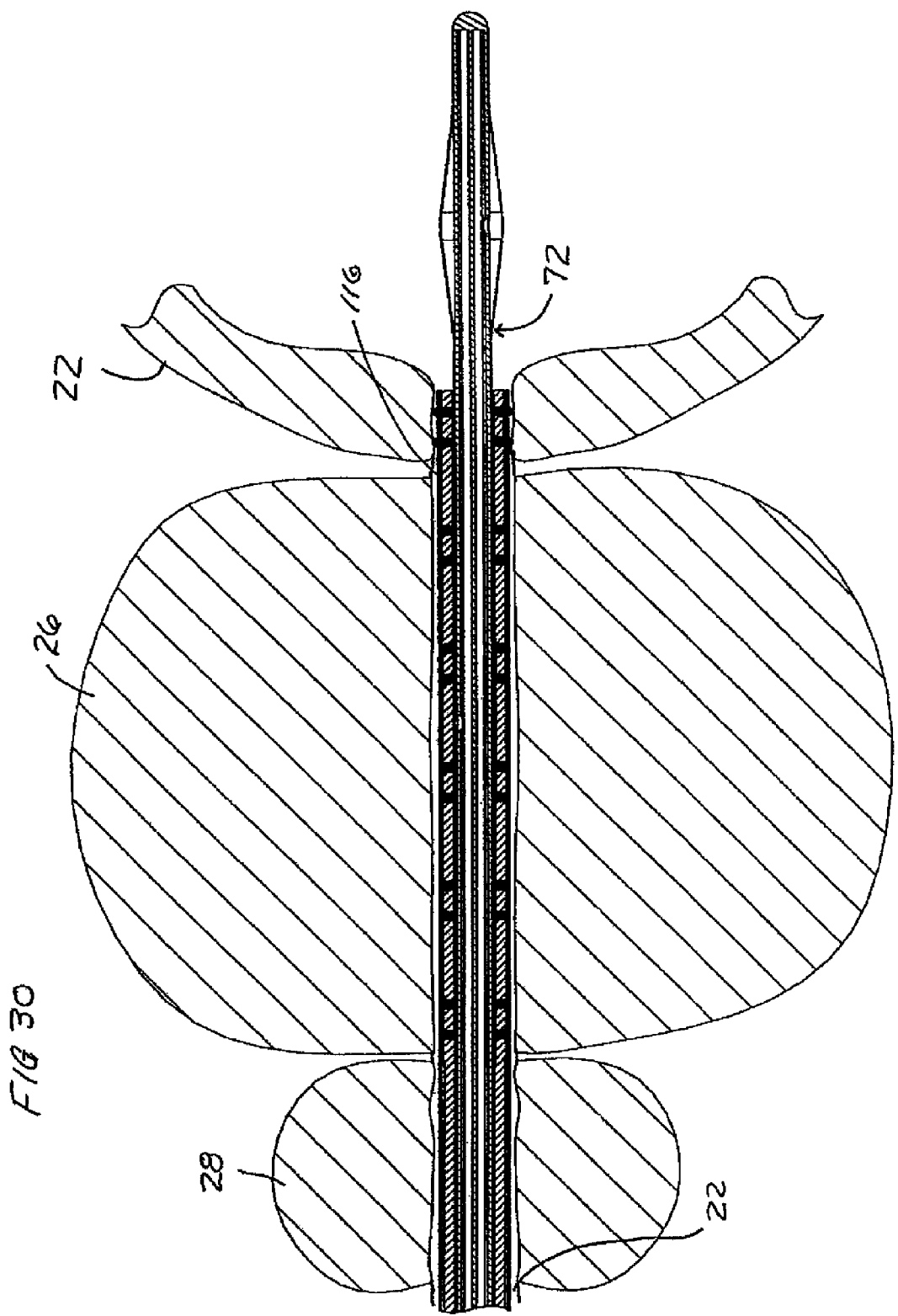

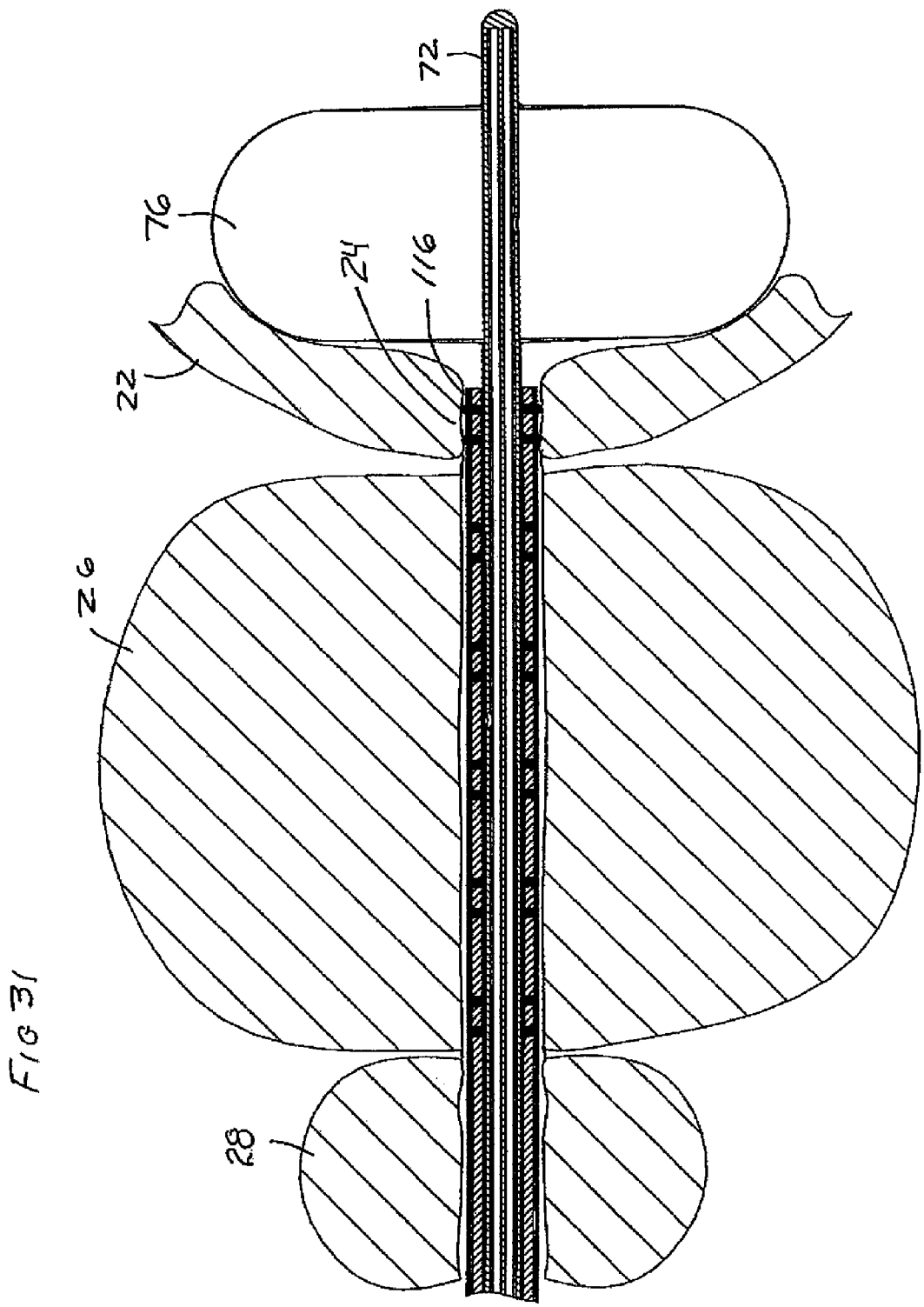

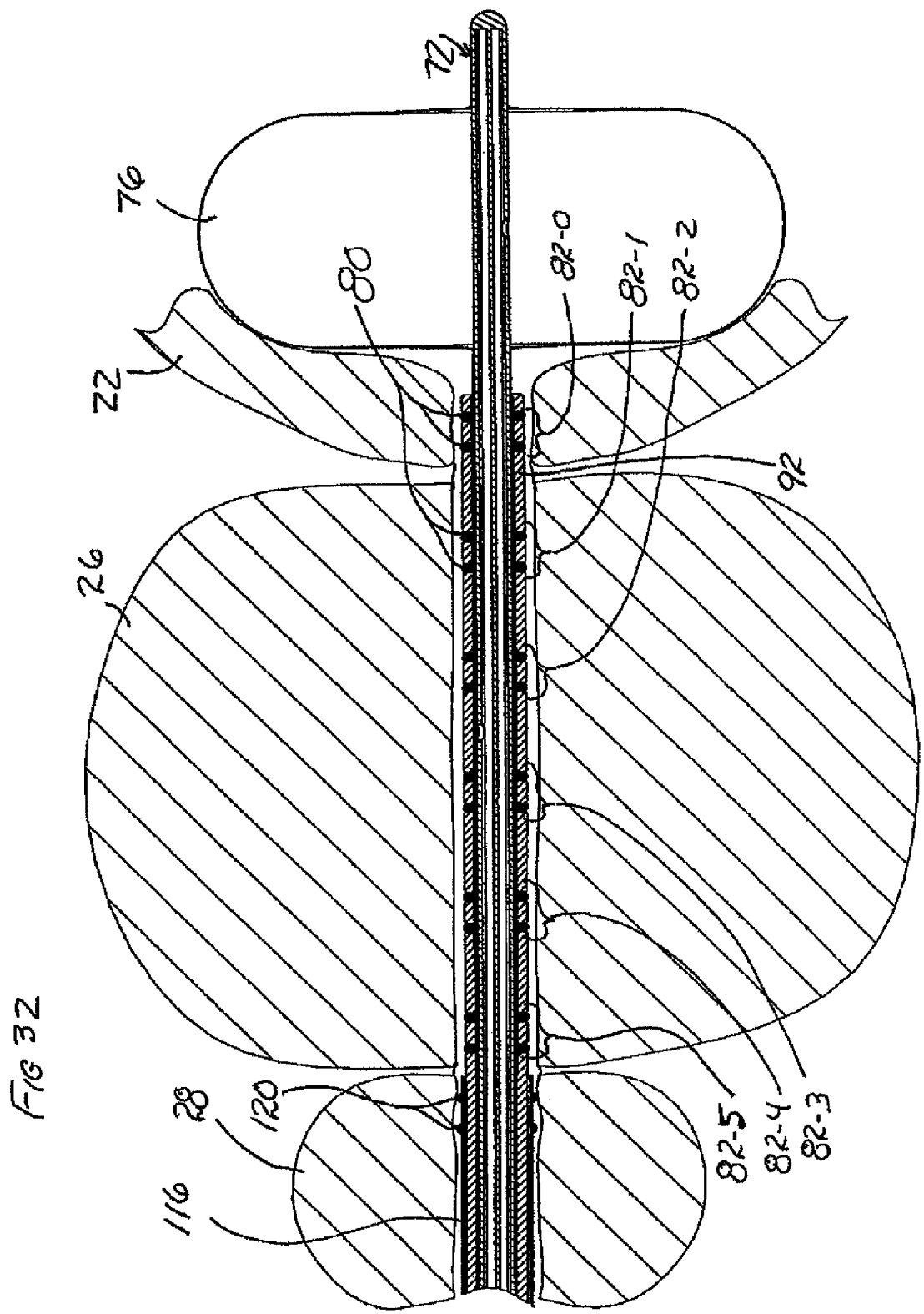

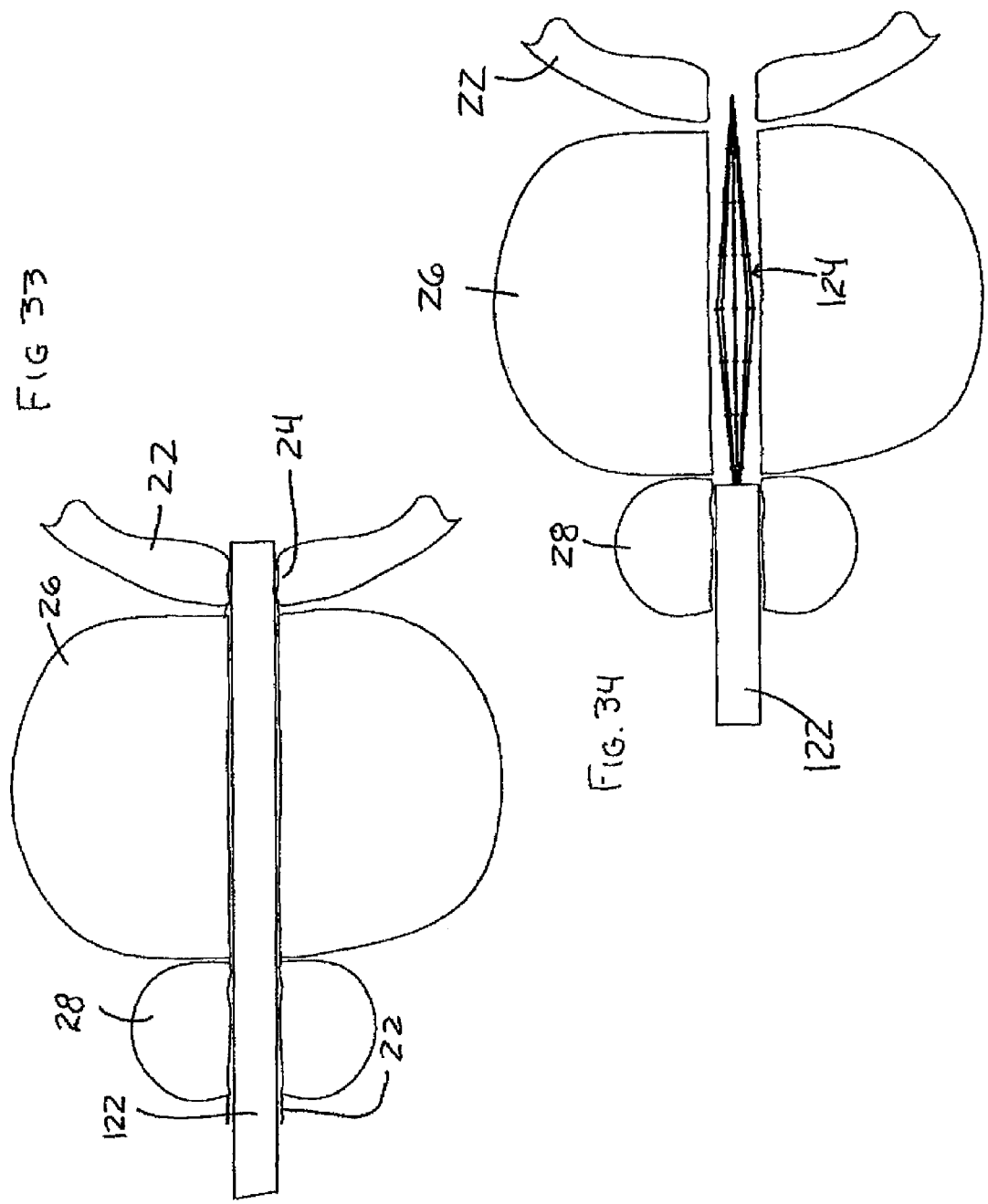

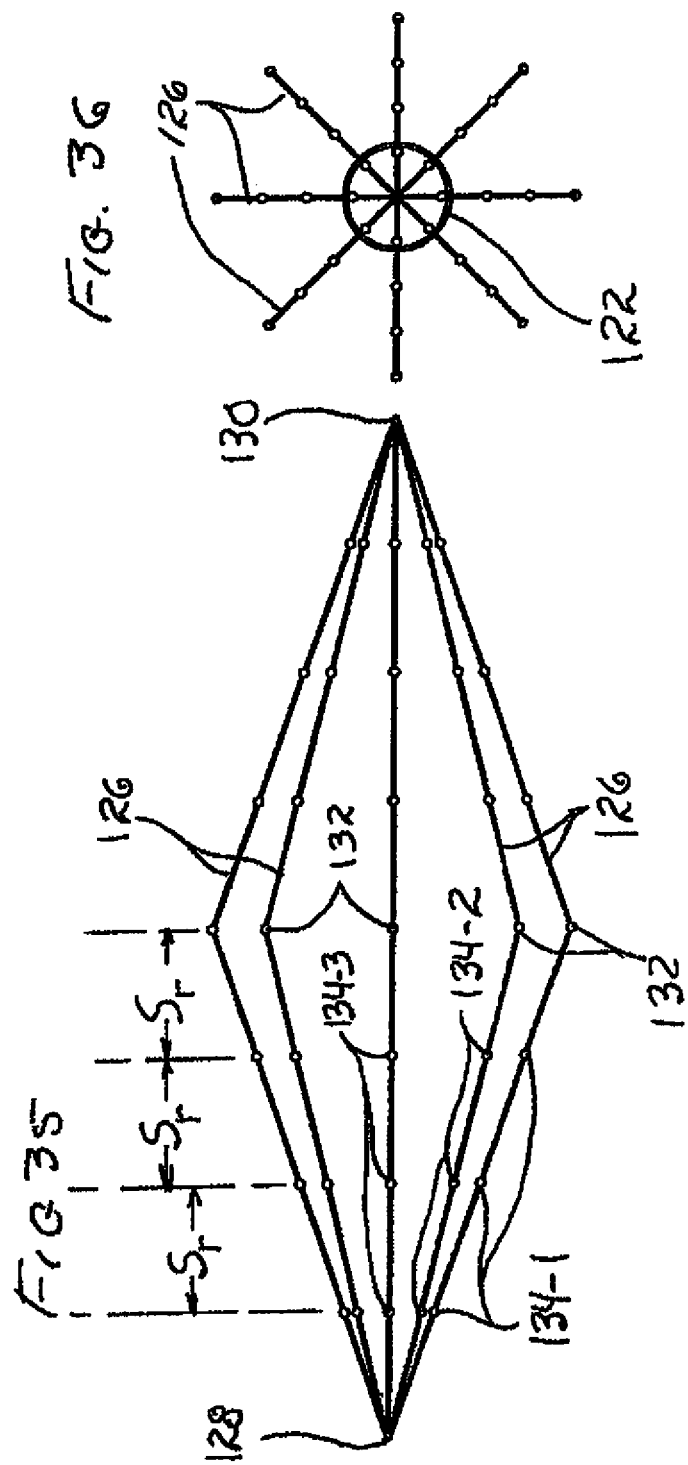

METHOD AND APPARATUS FOR REMODELING/PROFILING A TISSUE LUMEN, PARTICULARLY IN THE URETHRAL LUMEN IN THE PROSTATE GLAND

CROSS REFERENCE TO RELATED APPLICATIONS

This application is the U.S. National Stage of International Patent Application No. PCT/US2011/062586, filed Nov. 30, 2011, which claims the benefit of and priority to of U.S. Provisional Application Ser. No. 61/418,476, filed Dec. 1, 2010, both of which is are hereby incorporated by reference in their entireties.

TECHNICAL FIELD

The present description is directed to methods and apparatus for remodeling and/or profiling a tissue lumen and, more particularly, the lumen of the urethra through the male prostate gland to treat, for example, benign prostatic hyperplasia.

BACKGROUND ART

Benign prostatic hyperplasia, or BPH, refers to the benign enlargement of the prostate gland, which usually occurs as a male ages. It is very common, and sometimes is also referred to as benign prostatic hypertrophy or simply an enlarged prostate.

The prostate gland surrounds the urethra and is located between the bladder and the penis. As the prostate enlarges with age, it can result in a narrowing or blockage of the urethra. This can cause more frequent urination, as well as other changes or problems if urine is retained in the bladder. Retention of urine within the bladder can strain the bladder, lead to urinary tract infections, bladder and/or kidney damage, bladder stones and, potentially, incontinence. Severe BPH can result in even more serious conditions.

There are a limited number of surgical treatments at the present time for BPH. One treatment is referred to as transurethral resection of the prostate (TURP), in which a resectoscope is inserted through the penis into the urethra. The resectoscope employs an electrically charged wire loop to cut and remove obstructing prostate tissue.

More recently, laser surgery techniques have been used, which employ a side-firing laser to vaporize the obstructing prosthetic tissue. Although laser surgery results in relatively little blood loss as compared to TURP, it is difficult to control and the long term effectiveness is not known, as tissue regrowth may occur.

There is also a procedure sometimes referred to as a transurethral needle ablation (TUNA). This procedure involves cystoscopically placing needles into the prostate and using low-level radio frequency ('RF") energy to create selective lesions that are later reabsorbed. Another procedure for treating BPH employs transurethral microwave procedures to heat selected portions of the prostate that are later reabsorbed.

Despite the efforts to provide improved alternative surgical techniques and apparatus, at the present time TURP is often the surgical procedure of choice. Notwithstanding drawbacks with TURP, including the necessity for anesthesia and significant morbidities such as blood loss (with the need for transfusions), incontinence and retrograde ejaculation, it provides relatively long-lasting flow improvement. Compared to the other available procedures, TURP is still considered by some to be the "gold standard" against which other procedures are compared. Accordingly, there continues to be a need for development of new apparatus and methods for treating BPH.

Patents describing microwave, bipolar ablation and other techniques for treating BPH, including attempted creation of a biological stent, include U.S. Pat. Nos. 5,992,419; 5,330,518; 5,509,929, 5,234,004, and 6,638,275. Description of related devices or methods is also found in Chapter 4 of "New Frontiers in Medical Device Technology," 1995, entitled "Localized Heating of Deep-Seated Tissues using Microwave Balloon Catheters" by F. Sterzer.

SUMMARY OF INVENTION

This description is directed to methods and apparatus useful in or suitable for profiling and/or remodeling and enlarging tissue lumen in the human body and, more specifically, the urethra within a prostate gland, as a treatment for BPH.

In accordance with one aspect of the method and apparatus described more fully below, the urethra is enlarged by a balloon or other expandable structure inserted into the urethra, and RF (preferably bipolar) electrical energy or other suitable energy is applied to the prostate via one or more desiccators or energy emitters that may be located on the surface of or within the expandable structure in a predetermined pattern or arrangement to heat the tissue and create a support framework or structure of higher density, stiffer tissue which resists closure of the urethra.

All of the physical changes in the tissue that result from energy source heating are not fully known, but it is understood that the use of radiofrequency (RF) energy results in desiccation of the tissue and cross-linking of proteins in the tissue, increasing the density of the tissue and causing it to shrink. The tissue becomes stiffer than normal and more resistant to deformation. For purposes of this description, such tissue may be referred to interchangeably as "treated" or "high density" or "denser" or "desiccated" or "cross-linked" tissue. The same tissue is referred to regardless of the terminology used. As noted above, the heating is preferably but not exclusively carried out using radiofrequency (RF) energy, and particularly bipolar RF energy, applied to one or more desiccators carried by the expandable structure, which creates current flow through the tissue contacting the desiccators(s). The desiccator(s) are preferably electrically conductive and may be one or more electrodes or electrode groups or series, such as electrode pairs. The pattern of lines or points of desiccated tissue within the lumen is configured to create a support structure or bridge in the natural tissue of the prostate and/or urethra in which the stiffer treated tissue tends to hold the urethra lumen open in the expanded condition and is resistant to lumen closure.

The present subject matter also includes apparatus and methods for identifying, monitoring and/or profiling tissue along the urinary tract according to one or more characteristics of tissue. More specifically, such method and apparatus, which may be embodied in the apparatus described above or in separate additional apparatus, and may be employed to identify tissue and/or generate a profile of tissue in the male urinary tract. For example, in the treatment of BPH, such method and apparatus may be used to provide information or generate a profile of an electrical characteristic of the tissue, such as impedance, that allows the medical professional to identify different areas of tissue, such as bladder, bladder neck, prostate and urethral sphincter tissue, based on different electrical characteristics such as impedance characteristics of the tissue. As described in more detail below, such information may be employed separately or in combination with the treatment apparatus and methods identified above for determining the particular size of an individual's prostate, selecting appropriately sized treatment apparatus, gauging or verifying proper treatment location, determining treatment energy or time, verifying completion of the treatment and/or protecting sensitive tissue such as the urethral sphincter during treatment of the prostate, or any combination of these.

In accordance with one aspect of the present subject matter, apparatus is provided for remodeling a tissue lumen. The apparatus may include an elongated shaft having proximal and distal end portions; an expandable structure located at the distal end portion and movable between an unexpanded or retracted position for insertion into and withdrawal from the lumen and an expanded position for enlarging a selected portion of the lumen; at least one tissue desiccator carried on the expandable member(s) in a preselected configuration for contacting lumen tissue when the expandable member(s) is expanded; and wherein the preselected configuration is operable to define in the lumen tissue a support structure of desiccated tissue that resists closure of the lumen.

In accordance with further aspects, the "expandable structure" is not limited to a single structure or member and may include one or more balloons, baskets, cages and/or open frameworks, although the structure is preferably at least one balloon that is insertable into a lumen in the deflated condition and then inflated to enlarge the lumen and subsequently deflated for withdrawal. The expandable structure may be of uniform cross-sectional size or diameter or also include a plurality of regions that expand to different sizes. For example, the expandable structure may define or include proximal and/or distal portions of one or more selected diameters or cross-sectional areas and an intermediate portion of greater or lesser diameter or cross-sectional area. For treatment of BPH, for example, the apparatus preferably is elongated, with a length sufficient for insertion through the human male urethra and the prostate gland, and the expandable structure is elongated and/or may be sized such that the proximal and distal portions reside, when inserted into the urethra, at the vicinity of the bladder neck and urethral sphincter respectively, and the intermediate portion (which may be of larger inflated size than the proximal and/or distal portions) is located within the prostate gland.

"Desiccator" is intended to refer to any structure that desiccates the lumen tissue, including energy emitters/receivers of various types and electrodes of any suitable shape or size. The apparatus includes one or more desiccators for heating and desiccating lumen tissue and may include a plurality of desiccators, which may be spaced apart on the expandable structure. More specifically, the apparatus may include a plurality of conductive electrodes or electrode groups or series, such groups or series being spaced apart. "Groups" or "Series" refers to a plurality of desiccating members or electrodes such as two, three or more that are arranged in proximity, but still spaced apart to allow voltage to be applied between individual electrodes of a given group or series. If each group or series is a pair of electrodes, for example, each electrode pair may be attached to an energy source for heating the adjacent tissue—e.g., creating a voltage between the individual electrodes of each pair and delivering energy (e.g., electrical current) through the tissue generally located between the electrodes of each pair, heating the tissue and thereby forming a region of desiccated high density tissue between the electrodes of each pair. The location of the group or series on the apparatus may thus be identified as a desiccation region or zone. A generator, such as an RF generator, which may be included as part of a system with the apparatus or may be separate, may be configured to deliver the same level of energy to each desiccator, e.g., electrode or electrode series, or optionally the energy level may differ among the desiccators and further optionally may differ according to sensed characteristics of lumen tissue proximal to each desiccator.

The at least one desiccator is preferably operable to desiccate tissue of the lumen and/or tissue around the lumen to support the lumen in an open condition. More preferably, the at least one desiccator is configured to form a supporting pattern or arrangement of desiccated tissue or ablation lines in the lumen tissue which tend to hold the lumen in an open configuration. In one embodiment, the desiccators are located so as to form a plurality of annular rings or hoops of desiccated tissue along the length of the lumen to support the lumen in a open position. The desiccator may be point sources of energy or may be serial or continuous sources such as elongated electrodes. The desiccators are preferably, but not exclusively, expandable to expand as the expandable member is expanded.

In another and independent aspect of the present subject matter, apparatus is provided for developing a tissue profile along a body lumen, for example, the urethra. The tissue profile may be a profile of a selected electrical characteristic of the tissue, such as impedance or resistance. Such apparatus may include an elongated shaft sized for insertion into the lumen in question, and at least one and preferably a plurality of sensing zones or stations spaced apart along the shaft for contacting tissue of the lumen. Each zone or station preferably includes an electrode and more preferably a group or series of electrodes, such as a pair of proximal but spaced electrodes. The apparatus also may include a monitor/sensing apparatus in electrical communication with the sensing stations for monitoring an electrical characteristic of tissue in contact or in proximity with the sensing stations. The monitor may include a user interface for communicating the sensed electrical characteristic to the user. Together, the sensed characteristics from the sensing stations provide a profile of the characteristic along the lumen, which may be employed in subsequent treatment to enhance effectiveness and/or reduce the risk of error. If the shaft has a single sensing station, the electrical characteristic of the tissue may be monitored as the shaft is inserted and correlated with the location of the sensing station within the lumen, e.g., the distance of insertion, to provide the tissue profile.

Specifically, the monitor may be configured to sense the resistance or impedance of tissue located at or in proximity to each electrode or electrode pair (at each sensing zone or station). For example, the monitor may include a generator and be configured to create a known voltage between the individual electrodes of each pair and to measure current flow therebetween, from which the impedance or resistance of the tissue between the electrodes may be determined. The values of all the sensing stations or the single station along the insertion track may be compiled by the monitor in graphical or pictorial display for the user to visualize the tissue profile along the lumen. This information may be employed by the user in treating BPH, for example, to identify particularly sensitive areas or structures, such as the bladder neck or urethral sphincter, where those electrical characteristics are understood to differ. The apparatus here may be freestanding or may be combined as a single or integrated apparatus/system with the treatment apparatus described above.

The present subject matter also includes methods for treating and methods of profiling tissue of a lumen. In one aspect, a method for remodeling a tissue lumen is described that comprises: enlarging a selected length of the lumen; and desiccating tissue of and surrounding the lumen while it is enlarged, in a predetermined pattern that resists closure of the lumen.

The lumen may be enlarged by expanding an expandable structure within the selected length of lumen. The lumen tissue may be desiccated by, inter alia, heating it. In one example, the desiccated tissue comprises a series of high density tissue rings located along the lumen, although any suitable reinforcing or bridging configuration or arrangement or pattern along the lumen tissue and therearound that resists closure may be used.

More specifically, the method of remodeling may comprise inserting an expandable structure into the selected length of lumen, the expandable structure carrying at least one desiccator, e.g., electrode, defining the predetermined pattern, and expanding the expandable structure to enlarge the lumen and contact lumen tissue with the at least one desiccator, and energizing the at least one dessicator with, e.g., radiofrequency energy, to heat the lumen tissue in contact with the at least one desiccator. The selected length of tissue lumen may be the lumen of a urethra within a prostate gland, and the at least one desiccator may include a plurality of desiccators, such as electrodes or groups or series of electrodes, such as electrode pairs, located in spaced apart location along the expandable member.

Any of the above methods may include generating a profile of an electrical characteristic of tissue along a lumen such as the urinary tract or such profile may be generated separately and independently of the remodeling. The profile may be created by contacting tissue of the urinary tract with at least one electrode and preferably a pair of adjacent electrodes at spaced locations along the urinary tract and sensing the electrical characteristic (e.g., impedance or resistance) at such locations. The method may include applying a voltage between the electrodes and sensing resistance, impedance, voltage and/or current flow between the electrodes. Also the change or rate of change of any of the characteristics may be sensed or determined. Preferably, the electrical profile may be generated before any enlarging of the lumen and desiccating for remodeling purposes and may include a profile of tissue electrical characteristic, such as impedance, along the urethra.

Any of the above methods and/or apparatus for profiling and/or treating may include identifying prostate tissue by such electrical characteristic and/or distinguishing bladder neck tissue and/or urethral sphincter muscle tissue from prostate tissue based at least in part on the electrical characteristic.

Any of the above methods or apparatus for treating/remodeling and/or profiling may also comprise a sheath that is configured for insertion into the urethra, and optionally employing the sheath to protect the sphincter muscle by allowing the sheath to remain in the urinary sphincter as least temporarily during desiccation to separate the sphincter from any adjacent desiccators (electrodes) and protect the sphincter from substantial damage during desiccation of prostate tissue.

Any of the above methods of treating or profiling may employ any of the above apparatus for such treatment and/or profiling and, conversely, any of the above apparatus may be employed, as suitable, in carrying out any of the above methods of treating and/or profiling.

The above summary is for introduction purposes only. It represents a summary of only a few of the various features of the apparatus and methods disclosed herein and is not intended as a complete or comprehensive description or listing. The following more detailed description includes other features and functions.

DRAWING DESCRIPTION

Examples and embodiments of the present subject matter are set forth in the attached Figures, of which:

FIG. 3b is a side cross-sectional view of the catheter of FIG. 3a.

Figure 6:
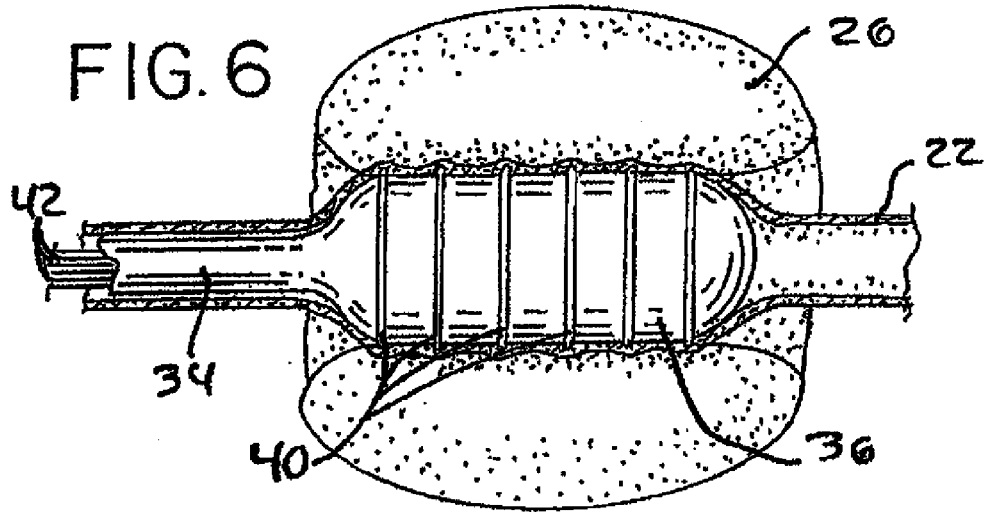
FIG. 6 is a cross-sectional view of the catheter of FIG. 5 with the balloon enlarged or expanded as part of a procedure for treating BPH.
Figure 7:
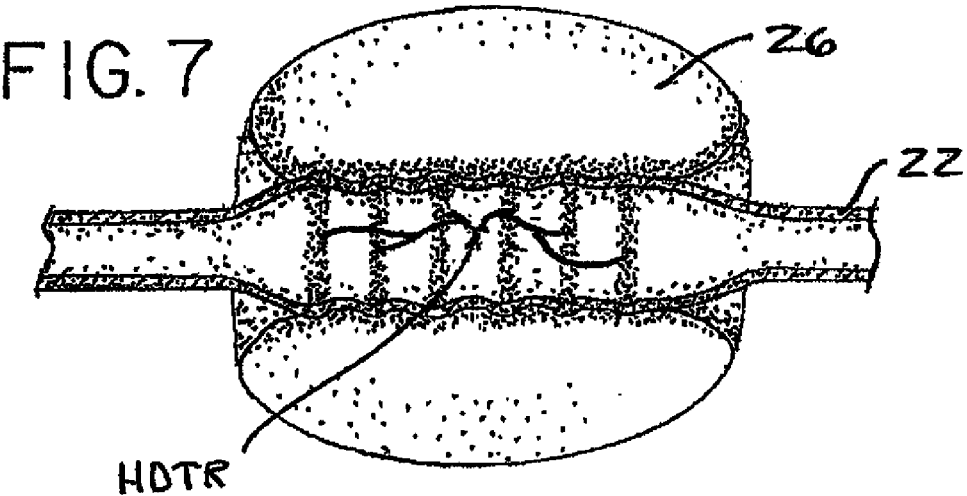

FIG. 7 diagrammatically illustrates the urethra within the prostate gland after treatment with the catheter of FIG. 6 and after removal of the catheter.

Figure 8:
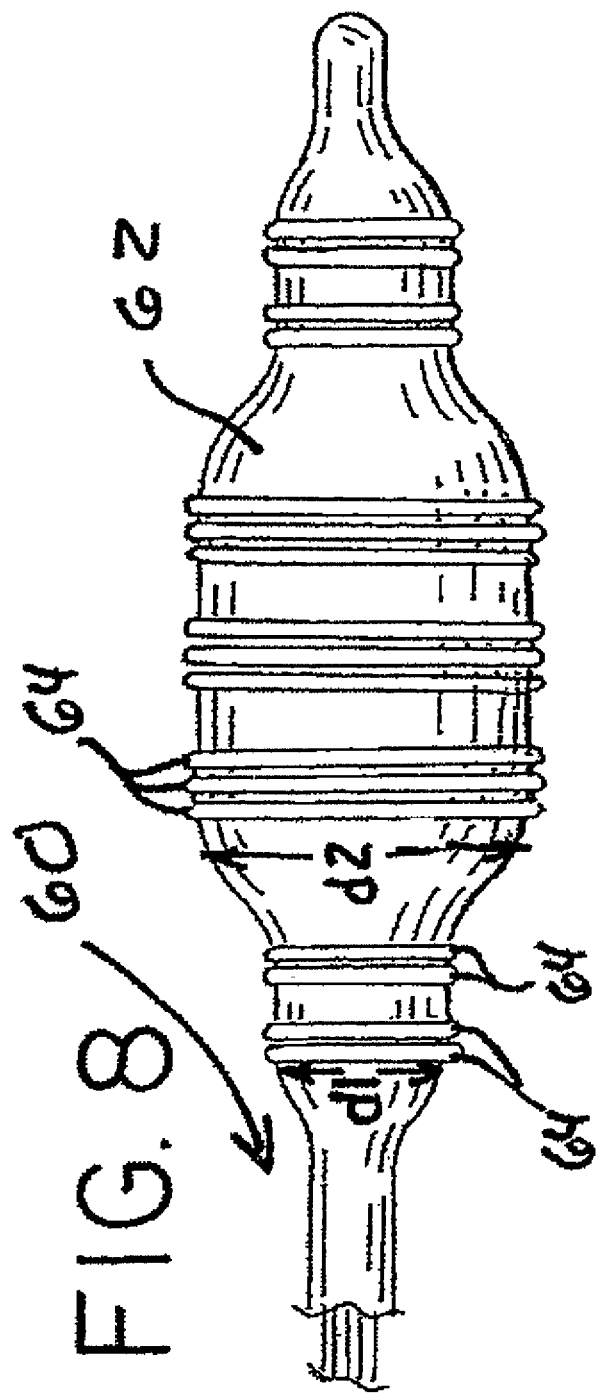

FIG. 8 illustrates a further alternative catheter embodiment, having an expandable member in the form of a balloon with differing diameters when expanded and a different electrode arrangement.

Figure 9:
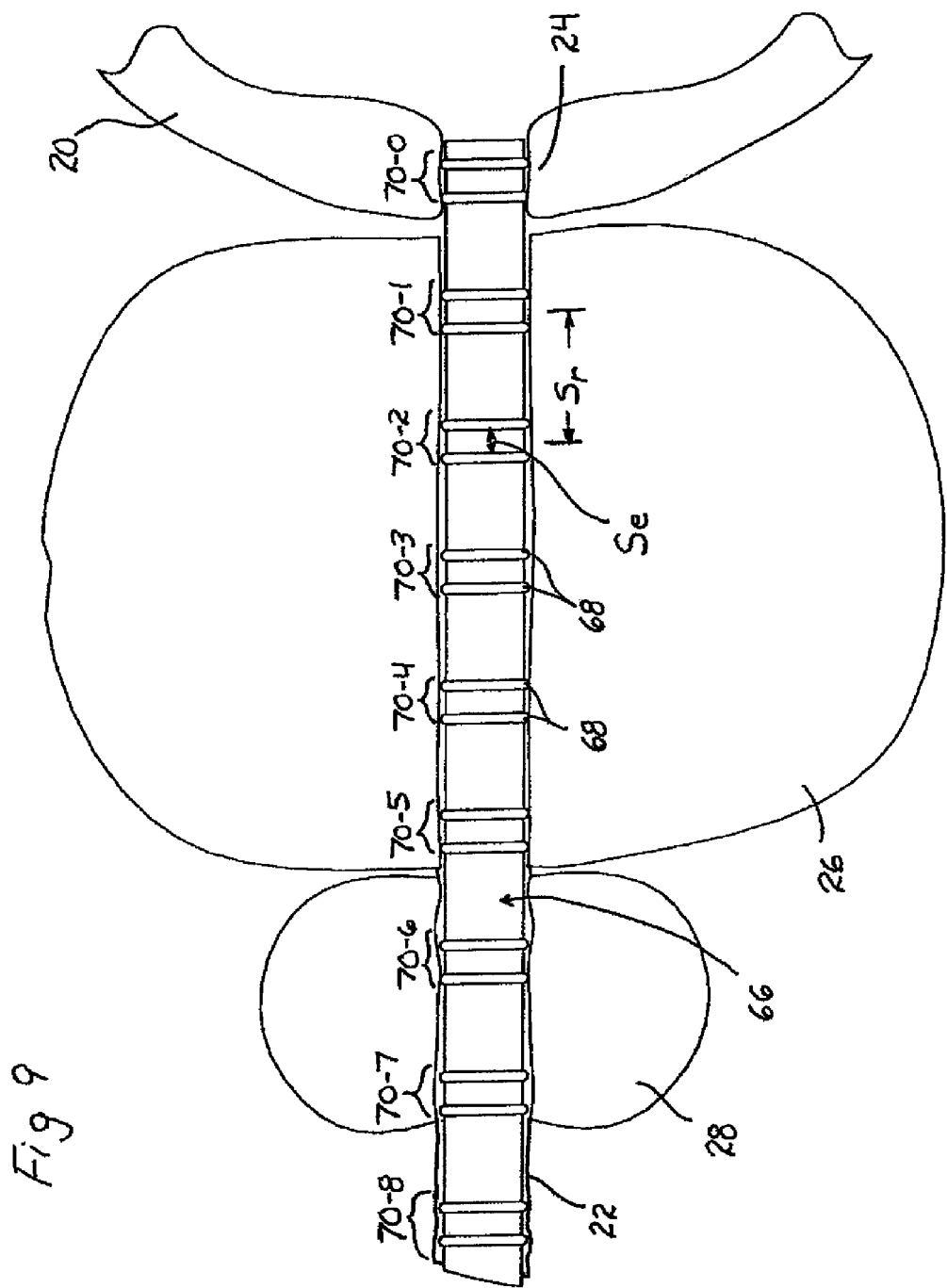

FIG. 9 is a cross-sectional view of the bladder neck, prostate and urethral sphincter with a separate measuring or profiling sheath, as described below, inserted into the urethra.

Figure 10:
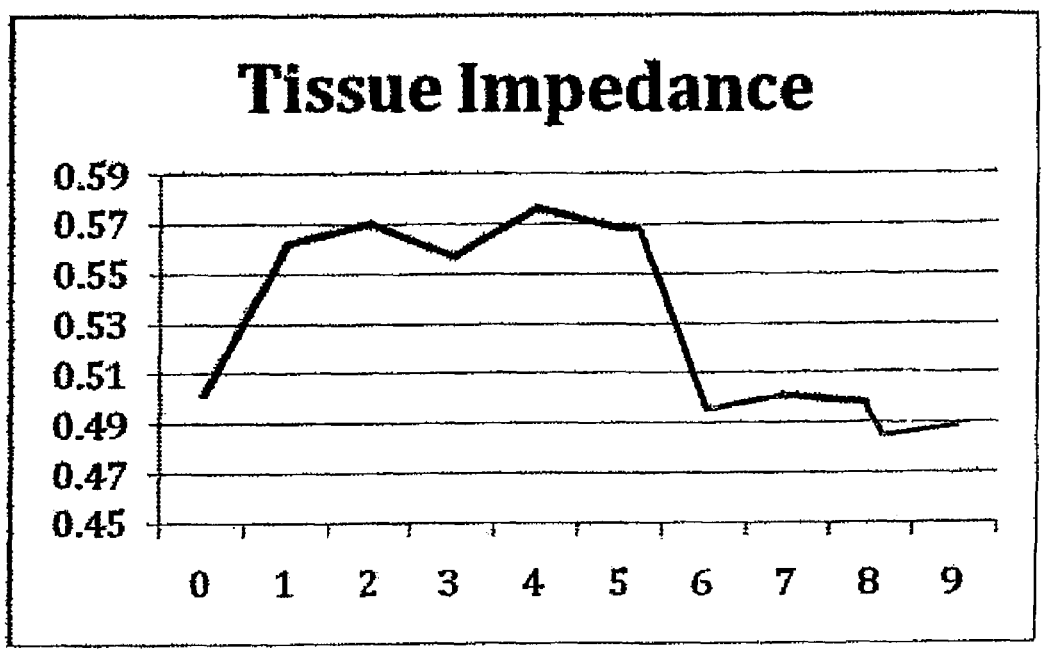

FIG. 10 is a readout or operator display interface in the form of a graph illustrating a possible tissue impedance profile along the urethra through the sphincter, prostate and through the bladder neck.

Figure 11:
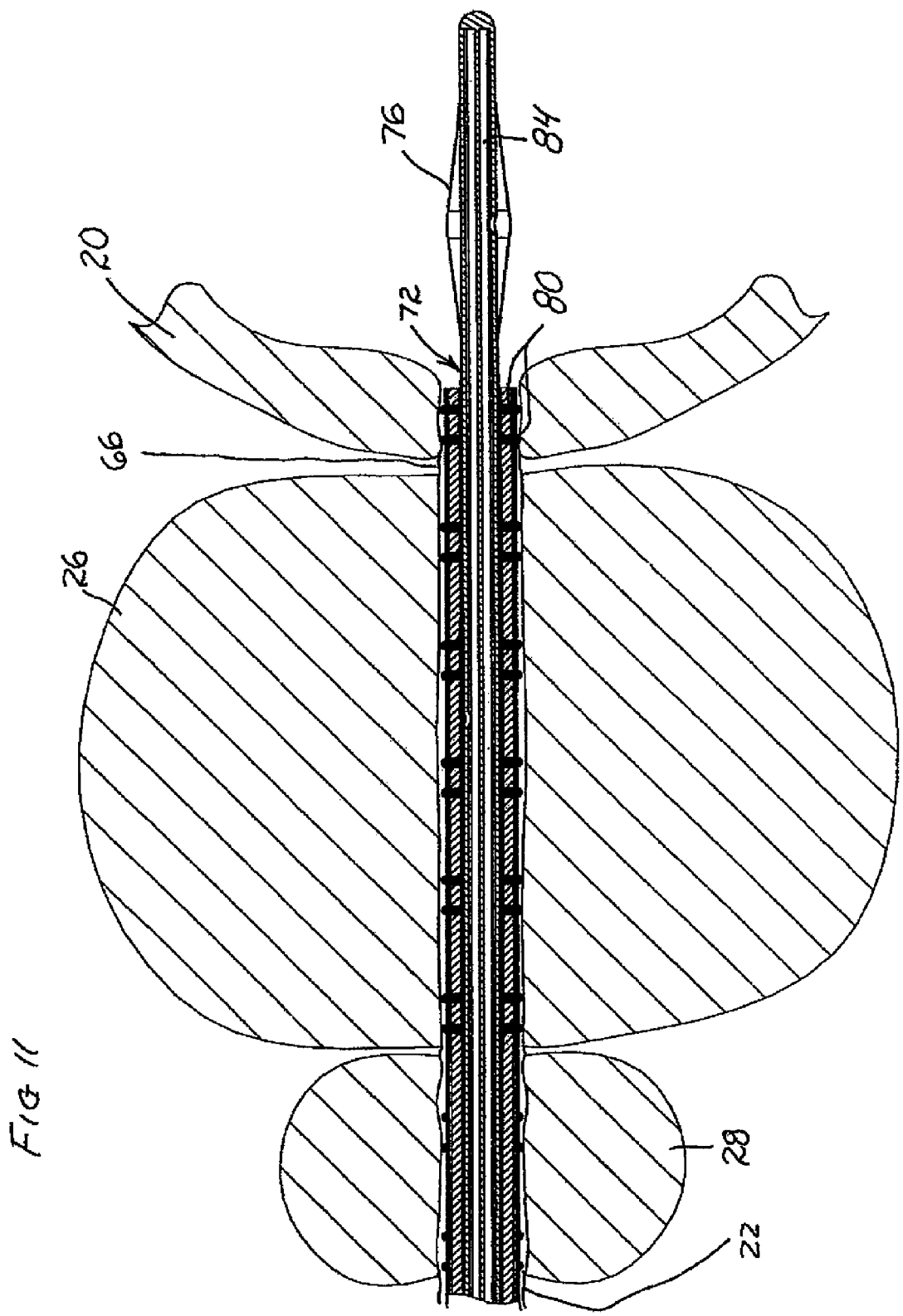

FIG. 11 shows a treatment device in the form of a catheter inserted through the sheath of FIG. 9 and extending through the sphincter, prostate and into the bladder.

FIG. 12 is similar to FIG. 11, with a distal expandable retention or bladder member, such as a balloon, expanded within the bladder.

FIG. 13 is similar to FIG. 12 but illustrates the sheath being withdrawn, exposing the distal portion of the catheter shaft and an expandable prostate or treatment member, such as a balloon.

FIG. 14 is similar to FIG. 13 but with the sheath withdrawn to a position contacting only the sphincter and covering the portion of the catheter within the sphincter.

FIG. 15 is similar to FIG. 14, but is a side view of the sheath and catheter and illustrates the treatment or prostate balloon, with a series of energy emitters such as bipolar electrode pairs on the treatment balloon, with the treatment balloon expanded within the prostate and the bladder or retention balloon expanded within the bladder, and further illustrates, by cross-hatching, a series of zones of relatively high density treated prostate tissue forming support rings or hoops in the prostate tissue to resist collapse of the urethral lumen to the restricted flow condition and to help support the urethral lumen in an expanded, less-restricted flow condition.

FIG. 16 is an isolated view of the treatment balloon portion of the catheter of FIG. 15 in the expanded or treatment condition.

FIG. 17 is an enlarged partial cross-sectional view taken along line B-B of FIG. 16, showing a portion of an electrode and a cross section of an electrode support structure located on the balloon surface, and a conduit run or lead passageway for electrically communicating with the electrode.

FIG. 18 is an enlarged partial cross-sectional view taken along line D-D of FIG. 16 and showing a portion of an electrode and another cross section of an electrode support structure located on the balloon surface and an electrical connection between the electrode and an electrical lead.

FIG. 19 is a perspective view of the treatment catheter in a position like that of FIG. 15, but with the prostate and bladder balloons removed for better visualization of the position of the ring-shaped electrodes and electrode support structure when the prostate balloon is expanded.

FIG. 20 is an enlarged isolation view of Detail E of FIG. 15.

FIG. 21 is a cross-sectional view of the treatment catheter and sheath as shown in FIG. 14, but with the treatment or prostate balloon also expanded and with the bladder, prostate, sphincter and urethra removed for clarity.

FIG. 22 is an enlarged view of Detail F of FIG. 21.

FIGS. 23A and 23B are perspective views of alternative expandable electrode pairs that may be employed on an expandable treatment member, such as a treatment balloon, in insertion or pre-treatment size and in expanded or treatment size, respectively.

FIGS. 24A and 24B are perspective views of further alternative expandable electrode pairs that may be employed on an expandable treatment member, such as a treatment balloon, in insertion or pre-treatment size and in expanded or treatment size, respectively.

Figure 26:
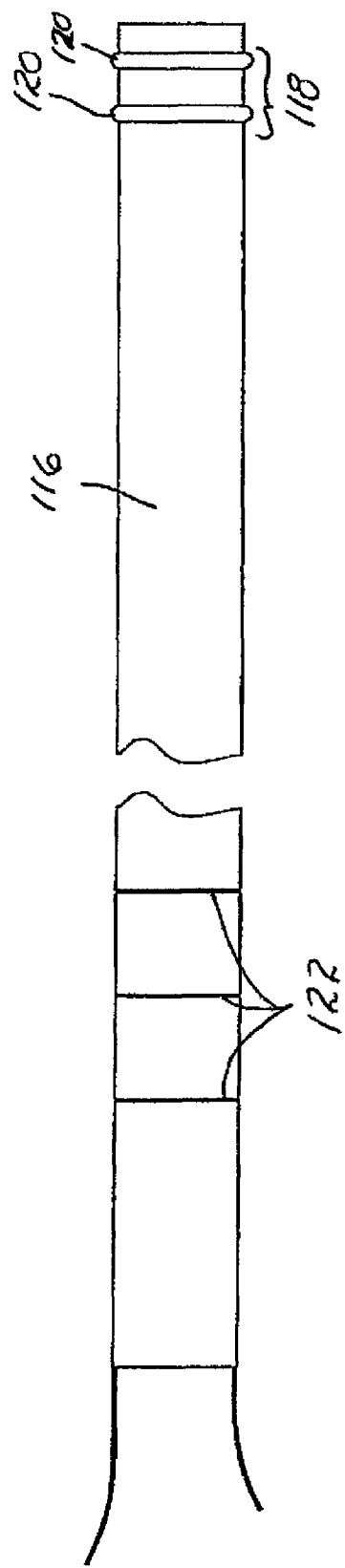

FIGS. 25A and 25B and top and perspective views, respectively, of a further alternative electrode design that may be employed in association with a treatment catheter for treating BPH FIG. 26 is a side view of a side view of an alternate embodiment of a measuring/profiling sheath with only a single energy emitter/sensor in the form of bipolar electrode pair located at the distal end thereof.

Figure 27:
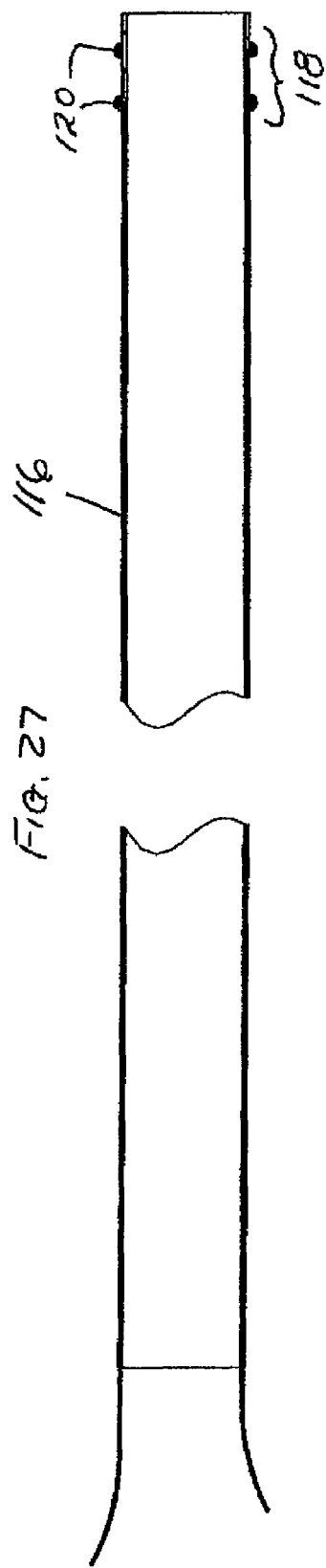

FIG. 27 is a longitudinal cross-sectional view of the sheath of FIG. 26.

FIG. 28 depicts the sheath of FIG. 26 positioned within a urethra of a male urinary tract and extending through the sphincter, prostate and into the bladder neck.

FIG. 29 is similar to FIG. 28, but shows the sheath as it is being withdrawn such as for establishing or confirming a tissue profile, with the distal end located in the prostate.

FIG. 30 shows a treatment catheter inserted through the sheath of FIG. 28 and extending through the sphincter, prostate and into the bladder.

FIG. 31 is similar to FIG. 30, with a distal expandable retention or bladder member, such as a catheter bladder balloon, inflated within the bladder.

FIG. 32 is similar to FIG. 31 but illustrates the sheath withdrawn, exposing the distal portion of the catheter shaft and an expandable prostate or treatment member, such as a balloon, and with the sheath overlying the catheter within the sphincter to protect sphincter tissue.

FIG. 33 shows an alternative structure in which guide sheath or introducer catheter is shown inserted into the urethra and extending through the sphincter, prostate and into the bladder neck for treating BHP.

FIG. 34 shows the alternative structure of FIG. 33 with the sheath withdrawn to expose an expandable structure in the form of a basket, cage, frame or a plurality of longitudinally extending wires with energy emitters or electrodes located on spaced apart positions on the wires, which wires are expandable to enlarge the urethral passageway through the prostate and bring the energy emitters into contact with the prostate tissue to permit the formation of high density support lines in the prostate, which help maintain the prostate in a more open, freer flow condition.

FIG. 35 is an isolated side view of the expandable cage or wire structure of FIG. 34 in an expanded condition.

FIG. 36 is an end view of the expandable cage or wire structure of FIG. 35.

DETAILED DESCRIPTION

Figure 1:
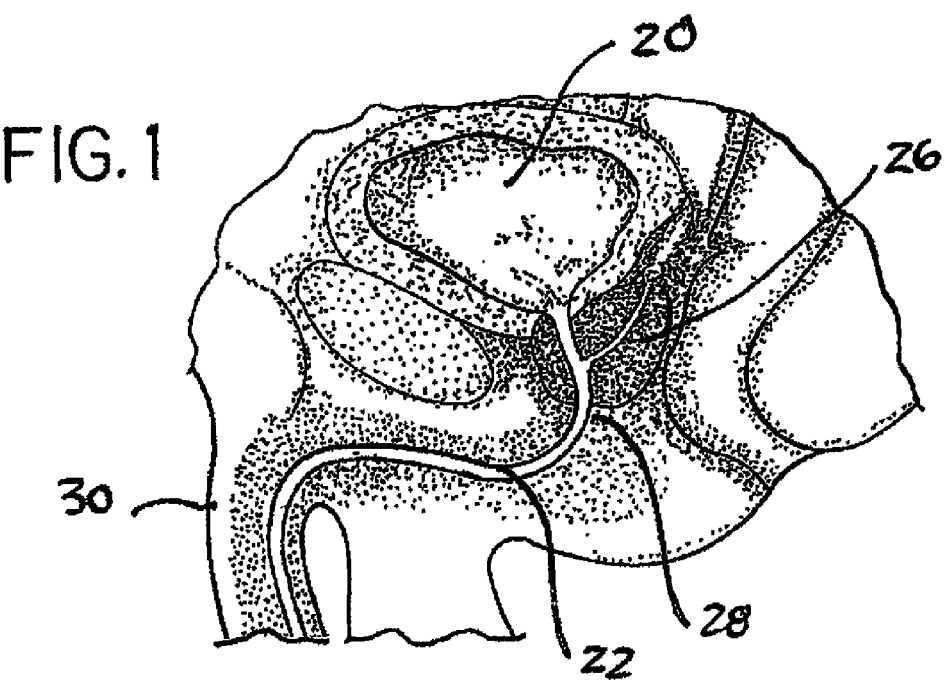
FIG. 1 is a cross-sectional view of the human anatomy, illustrating the male bladder, urethra and prostate in a normal condition.

Turning now to a more detailed description, FIG. 1 illustrates the normal anatomy of a portion of the male urinary tract, including the urinary bladder 20, which empties through the urethra 22. The urethra extends from a bladder outlet or neck 24, through the prostate gland 26, past the urethral sphincter 28, which controls flow, and through the penis 30. There are other related anatomical structures associated with the bladder, urethra and prostate, which are well known in the medical field and are not necessary for understanding the method and apparatus described herein.

Figure 2:
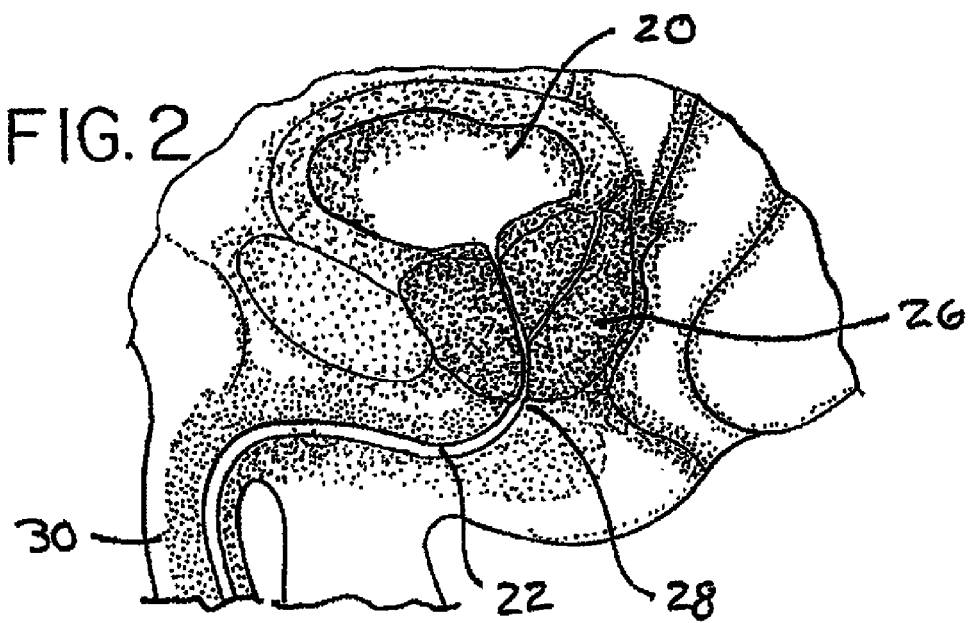
FIG. 2 is similar to FIG. 1, but illustrates the restriction or blockage on the urethra resulting from an enlarged prostate (BPH).

FIG. 2 is identical to FIG. 1, except that it illustrates the condition of the urethra when the prostate is enlarged, as from BPH, resulting in reduction of the lumen size and, in more extreme cases, potentially complete closure or obstruction of the urethra. In other words, as the prostate enlarges, it tends to push inwardly and close off or reduce the size of the portion of the urethra passing through the prostate glade.

Figure 3A:
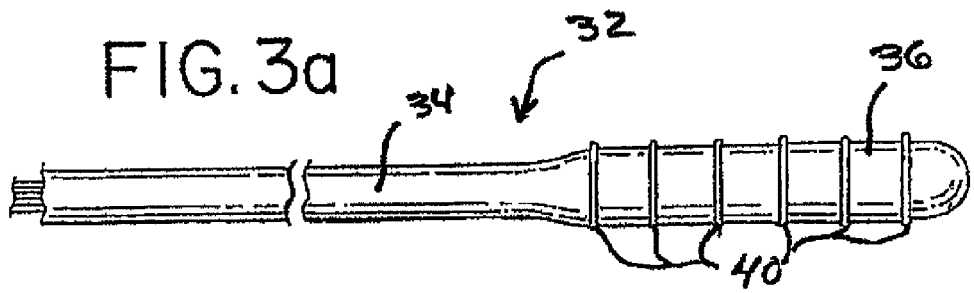
FIG. 3a is a side elevational view of a device in the form of a balloon catheter embodying the subject matter of the present description particularly suited for use in remodeling and enlarging the urethra within the prostate, which catheter employs an expandable member in the form of a balloon located on the distal end and a plurality of spaced-apart ring electrodes on the balloon.

FIG. 3*a* illustrates one embodiment of a treatment device in accordance with this disclosure that is preferably elongated and sized for minimally invasive insertion through the urinary tract and into the prostate. The treatment device is illustrated in the drawings as a catheter, generally at 32, which may be employed to treat BPH. A catheter is simply one form of a device that may be used to treat BPH as described herein. Other structures and devices employing an elongated shaft or member may also be used for introduction through the urinary tract. The illustrated catheter 32 includes an elongated shaft 34 made of polymeric or other suitable biocompatible material and of sufficient length to extend through the urethra from the distal end of the penis into the area of the urethra surrounded by the prostate gland.

To enlarge the prostatic urethra, the catheter 32 includes an expandable member or structure, which may be of any suitable form, such as one or more balloons 36, open frameworks, baskets or cage structures or other suitable expandable structures. In FIG. 3, the expandable structure is elongated and illustrated as the balloon 36, which may be enlarged from a diameter that closely conforms to the size of the catheter shaft for insertion through the urethra, such as a few millimeters or thereabouts, to a larger diameter, such as about a centimeter or larger so as to open, expand and enlarge the urethra within the prostate gland. The length of the balloon or other expandable structure preferably approximates the length of the prostate or slightly longer, which commonly varies from about 4 to 9 cm. Accordingly, a selection of treatment devices with expandable structures of different selected length and/or diameter may be provided for the medical personnel to select the appropriate size for a given patient.

The balloon 36 may be a single balloon or comprise multiple inflatable members or multiple cavities within a single balloon and may be securely attached or formed to the shaft in any suitable manner, which are well known in the urinary and cardiac catheter fields, including by adhesive, overmolding and other techniques. The balloon may also be of any suitable material, such as material that can withstand any increased temperature due to electrode heating. The balloon material may be either relatively compliant, such as silicone or urethane, or non-compliant, such a polyethylene terephthalate or PET, or of intermediate compliance. Preferably the balloon or other expandable structure is configured to expand to a relatively predictable maximum size. For a balloon, the material preferably is a relatively non-compliant such that the balloon can expand to a relatively predicable maximum diameter and resist further substantial expansion even upon increased pressure from an inflating fluid.

The balloon 36 may be of a single material or a laminate for the desired properties, and may be coated if desired with suitable agent, such as antibiotic, release agent, growth factor or other medication or agent to promote healing, enhance or retard cell growth, promote re-endotheliazation or for other therapeutic purposes, as may be desired. The balloon may also be non-expandable or stretchable in the usual sense, but made to full expanded size and wrapped or compressed around the shaft to assume a low profile during insertion and than expanded to full size upon inflation and reduced to smaller size for withdrawal by application of a vacuum after treatment is completed.

Figure 3B:
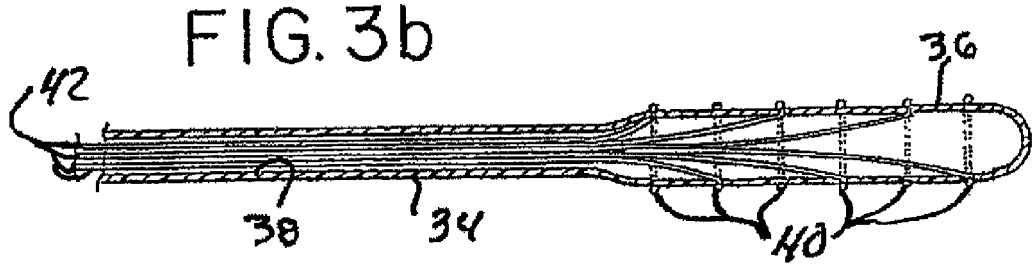

In the illustrated catheter, at least one inflation lumen 38 extends through the catheter shaft from the proximal end of the shaft to at least the balloon, and communicates with the area between the balloon and the catheter shaft at the distal end so that pressurized fluid, such as liquid or gas, can be introduced within the balloon to expand it. If multiple balloons or cavities are employed, multiple inflation lumen may be provided along or in the shaft. As illustrated, the expandable member or balloon 36 has at least one and preferably a plurality of desiccating zones or regions defined by energy emitters or receivers, such as desiccators or electrodes 40, in a predetermined pattern to create a natural support structure or bridge in the surrounding tissue that resists closure of the urethra. As illustrated in FIGS. 3a and 3b, a plurality of desiccators in the form of electrodes 40 extend circumferentially around the external surface of the balloon, and are located on the surface of the balloon at axially spaced apart locations, although other configurations or arrangements for the energy emitters (desiccators) or electrodes may be suitable, as will be explained more fully below.

The desiccators/energy emitters, and specifically the electrodes, may be formed in any suitable manner. For example, they may be in the form of conductive material imprinted or adhered to the surface of the balloon, or they may be separate structures, carried on the balloon and elastic or shape-formable to allow expansion thereof when the balloon is expanded and retraction thereof when the balloon is deflated. The desiccators/emitters electrodes may be of any suitable conductive material, such as copper, stainless steel, aluminum, gold or alloys, and may be coated (such as copper electrodes plated with a thin film of gold or silver) with any appropriate material, including metal or polymer, to enhance conductivity, reduce tissue adhesion, promote release or enhance other desirable properties.

As illustrated, the electrodes 40 (or other energy emitters or desiccators) are connected or are connectable to an energy delivery and/or sensing source, such as an RF energy generator and sensor (not shown) via conductors, such as wires 42 extending through the lumen of the catheter as shown in FIG. 3b. The RF generator may be either a monopolar or bipolar generator, although bipolar is preferred. In a monopolar application, the balloon electrodes 40 are connected to one of the generator voltage terminals or polarities, and the other voltage or terminal polarity is connected elsewhere, such as to a conductive pad upon which the patient lies. In a bipolar arrangement, as shown in FIG. 8 for example, one electrode 64 for an electrode group or series is connected to one of the terminals or polarities of the RF generator and an adjacent but spaced electrode 64 in the same group or series is attached to the opposite terminal or polarity. Because current flows between adjacent treatment electrodes in the bipolar arrangement, the amount and degree of tissue desiccation is potentially more easily controlled and limited in a bipolar than in a monopolar arrangement.

Figure 5:
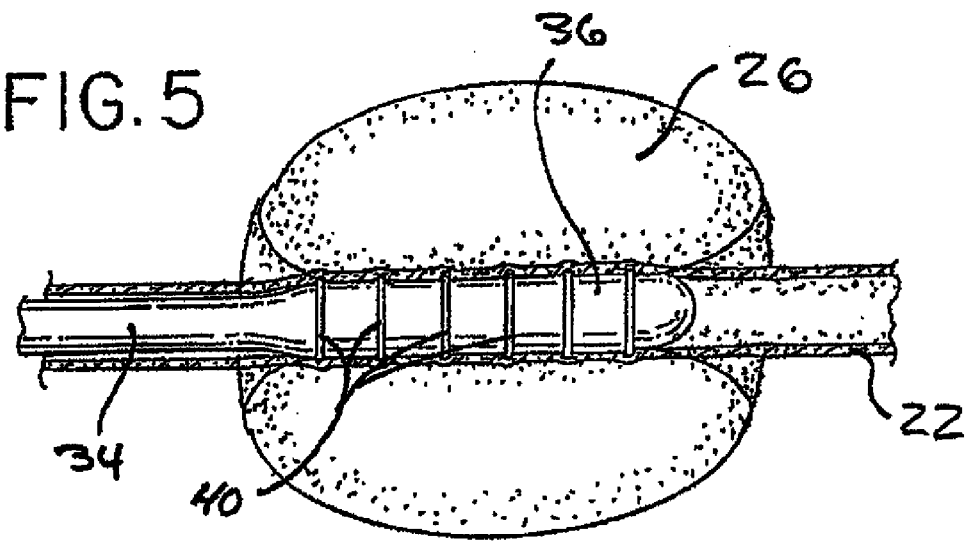
FIG. 5 is a cross-sectional view of a male prostate and urethra illustrating a catheter of FIG. 3 inserted into the urethra, and with the balloon located within the prostate gland.

A method of using the catheter of FIG. 3 to treat BPH is illustrated in FIGS. 5-7. FIG. 5 shows, in cross-sectional view, the catheter 32 of FIG. 3 inserted into the urethra lumen, with the balloon 36 located within the prostate gland 26. FIG. 5 shows the balloon 36 upon deployment into the urethra 22 but prior to expansion. FIG. 6 illustrates the catheter of FIG. 5 after the balloon 36 has been expanded, such as by the introduction of pressurized liquid or gas of suitable pressure, e.g., at up to about 50 psig or greater, through the catheter inflation lumen 38 and into the balloon 36. After enlargement of the balloon to the desired size and shape, which forms a comparably sized cavity within the prostate, and while maintained in the enlarged configuration, a voltage is applied from the RF generator, creating current flow between each of the electrodes 40 and a distant electrode (such as a stationary pad) in a monopolar arrangement.

Current flow through the tissue contacting each electrode 40 causes heating of the tissue, causing the tissue of the urethra and prostate in contact with and in close proximity to the electrodes to shrink and become more dense, forming a high density tissue ring or hoop (HDTR) that resists reclosure of the urethra. The current flow may be continued until sufficient time has elapsed or until impedance or other measurements, such as voltage or current, indicate that the tissue in contact and in proximity to the electrodes has been sufficiently desiccated or densified. It is anticipated that such tissue transition will take place in a relatively limited time such as a few minutes. Early preliminary tests achieved satisfactory results using about 15 watts of bipolar energy for about two minutes in testing of two circular electrodes in a bovine muscle tissue specimen. After the high density tissue rings (HDTR) are created, the electrodes are de-energized, the balloon deflated and the catheter withdrawn from the urethra.

After withdrawal of the catheter 32, as shown in FIG. 7, the treated tissue may be visualized as a series of circular high density rings (HDTR) of much denser urethral and prostate tissue axially spaced-apart along the urethra within the prostate gland. Because the rings of desiccated tissue have been formed in the expanded position their significantly increased density and stiffness as compared to normal tissue provides a support pattern or structure of tissue that resists the inward force from the enlarged prostate and tends to hold the urethra open and in a freer flow condition than before the treatment. Beneficially, this support structure or bridge is created from the natural tissues of the body itself and does not require the invasive tissue removal steps of the TURP or laser procedures, or the implant of an artificial structure or device.

More specifically, FIG. 7 illustrates a cross section of the urethral lumen in the prostate after the procedure has been carried out, showing that the tissue adjoining and proximal to each of the electrodes forms a ring or hoop of denser tissue (HDTR) which resists collapse and resists closing of the urethral lumen. Viable untreated tissue between the HDTRs may collapse slightly into the spaces between the rings, but the overall conformation of the lumen has been substantially enlarged and is maintained in the enlarged condition as a result of the spaced apart support rings created from the natural tissue of the body. It is believed that this untreated tissue will be useful to promote replacement of the natural endothelial tissue lining of the urethral lumen after treatment has occurred.

Figure 4A:
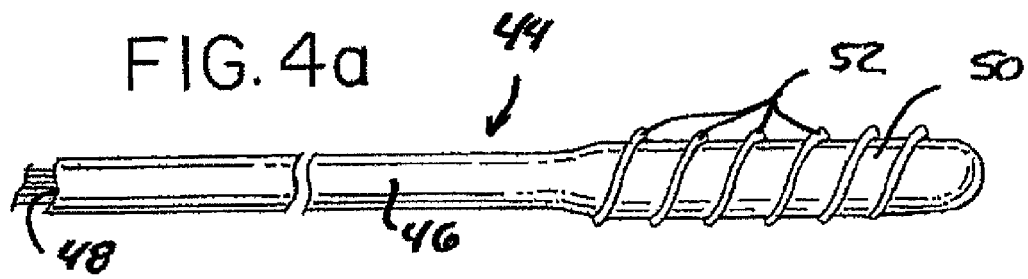
FIG. 4a is a side elevational view of catheter employing an alternative spiral or helical electrode arrangement.

Although illustrated in the above embodiment as a series of spaced apart electrode rings 40 around a balloon 36, the electrodes may be of any suitable shape and may be associated with any expandable structure, even an expandable structure comprised primarily of the electrode rings themselves, provided that they are configured to create lines of high density tissue that forms a support structure or bridge that tends to hold the urethral lumen through the prostate open and resist closure. For example, FIG. 4a illustrates a catheter 44 having an elongated shaft 46 with lumen 48 therein and terminating at the distal end with a balloon 50, similar to that described and shown previously in FIG. 3. However in FIG. 4a, an electrode is provided in a form of a continuous helical conductive member 52 disposed on the surface of the balloon. When the balloon is expanded and the electrode energized, the electrode will desiccate urethral tract and prostate tissue in a helical shape to create a support structure of higher density desiccated tissue to hold the lumen open in the manner similar to that described with the spaced apart HDTRs.

Figure 4B:
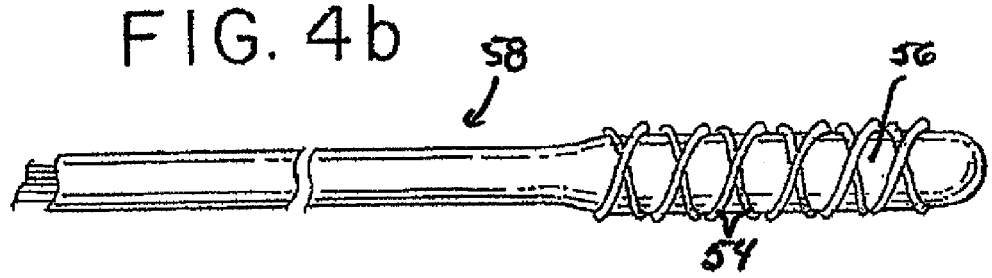
FIG. 4b is a side elevational view of another catheter employing a further alternative electrode arrangement using a pair of spiral or helical electrodes.

FIG. 4b illustrates an alternative arrangement in which electrodes 54 are located on the surface of a balloon 56 of catheter 58. In FIG. 4b, the electrodes are in the form of a pair of helical electrodes of opposite pitch, thereby forming opposed helical lines of treated tissue in the urethral lumen and prostate to support and hold open the lumen. Such electrodes may be energized simultaneously or at different times.

FIG. 8 shows yet another catheter 60, having a different expandable member or balloon and electrode configuration that is particularly suited for bipolar RF energy usage. In that embodiment, the balloon 62, when inflated has at least two different diameters or cross-sectional areas, a first smaller diameter d1 at the proximal and distal ends of the balloon and a larger diameter d2 therebetween. While the size, length and diameter of the balloon may vary, it is generally understood that for a typical prostate applications, the catheter and balloon, when uninflated, will preferably have a diameter of approximately 3-5 mm for insertion into the urethra. When the balloon is inflated, the large diameter d2 may be approximately 20-25 mm and the smaller diameter d1 at the proximal and distal ends may be about 10 mm, but preferably diameter d1 at the distal end is large enough to cause expansion of the bladder neck 24. The catheter may be provided with various different diameters and lengths of balloons for inflation, depending on the size of the urethral lumen and/or prostate in question, and the diameters at the proximal and distal ends of the balloon or other expandable member may also differ from each other.

As shown in FIG. 8, the electrode arrangement may also differ along the length of the balloon. The smaller diameter d1 proximal and distal sections are each shown with two series or pairs of electrodes 64. The electrodes of each pair are proximal but spaced-apart and the series or pairs themselves are spaced-apart a much greater distance. In a bipolar arrangement, the individual electrodes of each pair would preferably have opposite polarity so that current flows mostly between the electrodes in each pair instead of between electrodes of different pairs. The larger diameter d2 also could have a series of spaced apart electrode pairs, but is illustrated with plurality of spaced apart electrode groups or series having three adjacent but spaced electrodes 64 per group, with a larger space between individual groups. In a bipolar arrangement, the center electrode in a group could be of one polarity and the flanking electrodes in that group could be of opposite polarity—providing a HDTR of greater width than created by a single pair of electrodes. If a balloon such as shown in FIG. 8 were used in a monopolar application, all the electrodes on the balloon would presumably be of the same polarity and opposite to the polarity on the conductive patient pad—however the catheter in FIG. 8 is particularly suited to bipolar applications, which allow for better control of current flow between electrodes and reduced risk of undesired tissue damage. Various configurations or numbers or arrangements of electrodes may, of course, be used and still employ the features described and claimed herein.

Tissue Impedance Monitoring/Profiling

Experience in the prior art methods has demonstrated that it is highly desirable and yet often difficult to avoid damaging the urethral sphincter 28, which controls the flow of urine from the bladder. As explained in more detail below, one independent aspect of the apparatus and method of this description offers a unique and elegant advance relating to that issue. The present subject matter recognizes and takes advantage of differing tissue characteristics along the urinary tract. More specifically, method and apparatus are disclosed here for identifying, monitoring and/or profiling tissue along the urinary tract according to its response to electrical energy, for example by sensing or monitoring an electrical characteristic such as the tissue resistance or impedance or current flow through the tissue when contacted by an RF energized electrode or electrode pair.

The information thus developed may be utilized in BHP treatment, either separately or in combination with the treatment apparatus and methods identified above, for protecting the urethral sphincter against inadvertent damage or injury. But this information also has broader application and may be used, among other things, to determine the particular size of an individual's prostate, select appropriately sized treatment apparatus, gauge or verify proper treatment location, determine treatment energy or time, verify completion of the treatment and/or protect other sensitive tissue during treatment of the prostate, or any combination of these.

More specifically, it is understood that the urethral sphincter tissue will present different resistance to the flow of electrical current than does prostate tissue, and the prostate will have different characteristics than bladder tissue. By monitoring the electrical characteristics such as resistance, current flow or impedance the user and/or the system itself will be able to identify whether the particular electrode or electrode pair in question is located within the prostate or at the sphincter or at the bladder. More specifically, it is presently understood that a location within prostate tissue will be reflected by an impedance sufficiently different than the impedance at an electrode (or electrode pair) in contact with urethral sphincter tissue that it is detectable. This may be monitored visually by the user such as by viewing a meter, gauge, graph or electronic display of impedance, voltage, current or other variable and/or may be monitored automatically by the monitor/generator/sensing system.

As described in more detail below, such tissue identification can be carried out at any desired time, and entirely separately from treatment of BHP if desired. For example, the user can separately develop a profile of tissue along the urinary tract, such as a profile of tissue impedance of the bladder neck tissue, the prostate tissue and the sphincter tissue. This profile can help identify and distinguish the tissue and the size of the particular prostate, permitting more accurate selection of treatment apparatus of appropriate size and can help assure that sphincter tissue is protected from undue damage.

In addition, the identification and profiling can take place essentially simultaneously with or immediately preceeding the treatment, such as by a low voltage application of energy to the desiccators, emitters or electrodes for a profiling time period before treating, and/or by monitoring of impedance, voltage or current during treatment.

This information may also be utilized to automate the treatment procedure. In addition to better assuring that the proper tissue is being treated and that sensitive tissue is not being injured, the method and system can be employed for automated shut-off upon determination that desiccation is complete, for example via the monitoring of current or impedance at each electrode or electrode pair in accordance with the sensed tissue characteristic of the tissue in question. With this information, the system could de-energize each electrode or electrode pair as completion is detected. The generator/sensing unit could include a controller, such as with a programmable microprocessor, programmed to carry out the monitoring steps and activation, inactivation or alarm functions for the surgeon, as described above.

Tissue Profiling/BHP Treatment

Without limiting the various possible applications of the tissue characteristic identifying, monitoring or profiling described above, FIGS. 9 through 15 illustrate, in accordance with a particular example of the present subject matter, how a tissue profile may be developed to better assure that the balloon catheter is of appropriate size and or properly positioned to result in expansion of the desired structures, such as the prostate 26 and bladder neck 24, and to avoid expansion and or desiccation of tissue in the area of sphincter 28.

FIG. 9 illustrates a first step in one embodiment of the method described above. As shown there, an elongated hollow sheath 66, preferably with an internal dilator not shown, is inserted through the urethra 22, the sphincter 28, prostate 26 and into the bladder 20. As illustrated in this embodiment, the sheath includes a plurality of tissue sensors located at spaced locations along the surface of the sheath. More specifically, the sheath includes a plurality of electrically conductive electrodes 68 spaced along the sheath for sensing tissue impedance. The illustrated electrodes are generally circular or ring shape and extend around the surface of the sheath. They may be formed on the surface of the sheath, such as by deposit of a conductive film, or attached to the sheath in any desired manner. Because the sheath does not expand in the illustrated embodiment, the electrodes do not need to be expandable, and they each communicate with bipolar generator/sensing unit through individual conductors that extend preferably longitudinally through the sheath to the proximal end that is remains outside of the urinary tract. Other configurations of electrodes that are non-circular, such as point source, may also be employed.

Still more specifically, the electrodes 68 are preferably positioned on the sheath 66 in pairs 70, and a plurality of bipolar electrode ring pairs 70 define sensing stations or locations that are spaced along the sheath at specific intervals "Sr", such as one centimeter apart. For reference purposes, the number 70-0 designates the sensing station or electrode pair at the distal end of the sheath and located in the bladder neck 24 as illustrated, and each sensing station or electrode pair is sequentially numbered from there in a proximal direction along the longitudinal axis of the sheath, with electrode pairs 70-1 through 70-5 being located in the prostate, electrode pairs 70-6 and 70-7 being located in the sphincter, and pair 70-8 being in contact with the urethra proximal to the sphincter. The electrodes 68 of each pair 70 are preferably spaced apart distance "Se" of about 1-4 mm and each is connected, via conductors through the sheath (not illustrated in FIG. 9) for connection to opposite poles of a bipolar generator/monitor/sensor.

During insertion of the sheath, the tissue impedance (or other significant electrical characteristic of the tissue) between the electrodes of the distal most end pair 70-0 may be monitored and preferably the sheath is inserted until the distal most end electrode pair advances beyond the neck of the bladder and into the bladder. At that point the electrical relationship between the electrodes of the distal pair 70-0 should change significantly as compared to the electrical condition when they are in contact with tissue. For example, if the bladder has urine in it, it is anticipated that an impedance reading characteristic of urine will occur between the electrodes of the distal most pair, indicating entry into the bladder. Alternatively, if the bladder is empty, movement of the distal electrode pair from contact with the bladder neck 24 into the bladder itself should also be reflected by significantly increased resistance between the electrode pair, again reflecting insertion of the distal end beyond the bladder neck 24 and into the bladder. When this position is reached, the sheath is then retracted slightly until the sensed electrical condition between the electrodes of the distal most pair reflects a value, such as impedance, resistance or current flow that is indicative of contact of both electrodes with the tissue of the bladder neck 24, thereby indicating the position of the distal end of the sheath as shown in FIG. 9. For purposes of discussion, this position of the sheath will be referred to as the "tissue profile position".

Preferably the bipolar generator/monitor to which the sensing station electrode pairs are connected is a bipolar RF generator that also has an impedance, voltage, or current sensing and indicating capability, which determines the impedance or other electrical characteristic between the electrodes of each pair and generates a read out or display or alarm suitable for understanding or interpretation by the user. One example of such a read out may be a graph on an optical display or printed by way of an attached printing device.

As mentioned above, one method of generating a tissue profile is to evaluate the tissue as the sheath is inserted, monitoring the electrical characteristics between at least the distal-most pair 70-0 as the sheath is advanced. Tracking the tissue characteristic in relation to the distance the sheath is advanced will provide information giving the user a better understanding of anatomy of that particular patient, including an estimate of the length of the urethra and/or prostate.

Another approach to developing a tissue profile is employed after the sheath is positioned at the tissue profile position. After such position is reached, a slight bipolar voltage is applied between the electrodes of each electrode pair, and the impedance of the tissue between each electrode pair is sensed by the monitor/generator/sensing unit. As explained earlier, it is anticipated and understood that the tissue of the bladder neck, the tissue of the prostate and the tissue of the sphincter will each exhibit different impedances because of the different qualities and characteristics of the tissue, which differences will be detectable and can be presented in visual and/or numerical display.

For example, as shown in FIG. 10, a graph may be generated, with actual or relative tissue impedance along the ordinate or y axis and the relative location of the electrode pairs along the absyssa or x axis. With the distal most electrodes 70-0 representing position at location zero, and with each electrode pair being spaced a known distance apart, such as 1 cm, a profile may be generated of the tissue impedance (or other electrical characteristic) along the urinary tract. It is anticipated, for example, that the tissue impedance for the bladder neck will be different than a tissue impedance of the prostate, because of the different density and character of the tissue of the bladder neck. As the tissue impedance changes and is detected by the electrode pair 70-1 within the prostate, that change in impedance is reflected in the graph by, for example, an increase of the impedance or relative impedance (y axis) at position 1 on the X axis. It is further anticipated that the impedance of the sphincter will be different than the tissue of the prostate, such that the electrode pairs 70-6 and 70-7 located within the sphincter reflect a different tissue impedance in the graph at positions 6 and 7 along the X axis. Impedance may change further for electrode pair 70-8 proximal of the sphincter (position 8 on the graph). The increases and decreases shown in FIG. 10 are for purposes of illustration only, and significant information is reflected by reason of the change in the impedance or other electrical characteristic from one type of tissue to another and not necessarily whether it is higher or lower—although that information may also be useful.

Because the electrode pairs are a fixed distance apart, such as 1 cm, the user can identify the approximate length of the prostate from the graph and from that information select a catheter or other device having an expandable structure, as described early, of the appropriate length for that particular patient. For example, the tissue impedance profile illustrated in FIG. 10 would suggest that the distance from the distal electrode pair 70-0 to the electrode pair 70-5, which is the most proximal reading which appears to be of higher tissue impedance within the prostate is approximately 5 cm thereby providing valuable information to the surgeon for selecting a balloon catheter having a prostate expansion balloon or other expandable structure of the appropriate length for that particular patient.

After the sheath is positioned in the tissue profile position, and the tissue profile is established, the treatment device, such as a catheter 72 of the correct length is selected and, as seen in FIG. 11, the catheter may be inserted within and along an internal lumen of the sheath 66, whereby the catheter and sheath form, in combination, a treatment system. The illustrated catheter 72 has various components including an elongated shaft 74, a distal optional expandable bladder retention member or structure, such as a bladder retention balloon 76, located at the distal end portion of the shaft; an expandable treatment structure or member, such as prostate balloon 78 (which may also be called a urethral balloon), carried by the shaft proximal of the retention member or balloon; and a plurality of preferably expandable desiccators or energy emitters/receivers such as electrodes 80 positioned in electrode pairs 82 located on the treatment balloon and spaced apart the same distance as the electrodes and electrode pairs on the sheath 68. Although it is anticipated that the electrodes 80 will usually be expandable to accommodate expansion of the prostate balloon or other expandable member or structure, if the balloon is pre-formed such that is of full expanded size and simply wrapped or compressed about the shaft during insertion, electrodes that are film deposited on the sheath when it is full size will not be actually expandable in the same sense.

In use, the catheter 72 is inserted through the sheath 68 until the distal end expandable retention member or balloon 76 is located within the bladder 20, and the electrode pairs 82 are aligned with, or in registration with the electrode pairs 70 of the outer sheath 68. This positioning may be confirmed by alignment of proximal marking on the outer sheath and the catheter or by electrical sensing associated with the sheath and catheter electrodes 68 and 80. After the catheter is inserted, the expandable retention member or balloon 76, if present, is expanded, such as inflated by liquid or gas through inflation passageway 84 that extends longitudinally along the length of the catheter shaft 74, as shown in FIG. 12. It may be noted that since the catheter 72 has electrodes 80 located along the length of the catheter, the treatment catheter itself may be used for tissue profiling in essentially the same manner as the sheath, 68 and a sheath is not necessarily required although it is preferred for other benefits such as sphincter protection.

After the retention balloon is inflated or other structure enlarged, tension is applied to the catheter shaft to assure that the balloon or other expandable member is properly located adjacent to the neck of the bladder. At that point in the procedure, as shown in FIG. 13, the sheath 66 is gradually retracted proximally, sequentially exposing the bipolar electrode pairs 82-0 and others of the catheter to contact with tissue. The bipolar electrodes 80 communicate via conductors not shown in FIG. 14, with a bipolar generator and sensing unit which can apply a low voltage to the electrode pairs and sense the impedance of tissue contacting each pair. In this manner, the impedance between the electrodes pairs 82 of the catheter can be compared to the tissue profile originally created using the sheath 66, to verify that the electrodes of the catheter are properly positioned—for example, that the distal-most electrode pair 82-0 is located at the neck of the bladder and electrode pair 82-1 is located within the prostate and in contact with prostate tissue. The sheath may continue to be retrieved proximally, with the surgeon preferably monitoring the tissue impedance of the catheter electrodes to see that they correspond with the impedance previously sensed by the electrode pairs of the sheath.

As the sheath 66 is withdrawn, the impedance sensed by the distal pair of electrodes 70-0 on the sheath may also be monitored, and withdrawal continued until the sensed impedance on the distal-most electrode pair 70-0 of the sheath corresponds to the impedance that was sensed in the sphincter tissue by electrode pair 70-6 during the establishment of the tissue profile. This serves to confirm that the sheath is located over the catheter 72 in the region of the sphincter, as shown in FIG. 14, at which point withdrawal stops. This positioning of the sheath over the catheter within the sphincter aids in protecting the sphincter against unintended desiccation upon activation of the electrodes 80 of the catheter 72.

After the outer sheath 66 has been withdrawn to a position located within the sphincter, the treatment or prostate balloon 78 (which is located in the prostate and optionally the bladder neck) is inflated by pressurized liquid or gas, such as liquid under pressure of up to about 50 psig or more, through inflation lumen 84 which extends along the length of the catheter and through a side wall aperture 86 that communicates with the inside of the treatment balloon 78. As best seen in FIGS. 15, 16 and 19, this causes the balloon to expand, substantially, enlarging the urethral passageway through at least the prostate gland 26, creating an enlarged cavity in the prostate, and optionally also the bladder neck 24, while, importantly, the tissue of the sphincter is protected from tissue desiccation by the sheath 66.

After the surgeon verifies that the expandable treatment balloon 78 (or other expandable structure or member) is properly positioned and expanded, and that the sheath 66 remains in the desired position protecting the tissue of the sphincter 28, the electrodes 80 are energized, preferably with bipolar RF energy, the electrodes of each pair 82 being of opposite polarity thereby creating a current flow between the electrodes of each pair and through the adjoining urethral and prostate tissue along the balloon. Preferably the electrodes are energized with sufficient energy to create the desired desiccation, cross linking and shrinkage of the prostate tissue in the treatment zones 88 adjacent to each electrode pair, as illustrated diagrammatically in FIGS. 15, 19 and 20. Preferably, during the application of energy, each electrode pair is separately monitored and energized and the impedance is monitored multiple times per second. The same voltage may be applied to each pair of electrodes or the voltage may differ, for example, depending on the sensed electrical characteristic of the tissue such as impedance. When the tissue impedance at each desiccation zone or station at electrode series or pair has reached a value or plateau (or current flow has reduced) indicating that sufficient and preferably optimum cross linkage and shrinkage of prostate tissue has taken place and that energy delivery is no longer required, the RF generator may be turned off (or the energy switched off) for all the electrodes simultaneously or for each zone or group of electrodes individually as completion of desiccation is sensed at such zone or station. This may be done manually by the physician, for example in response to an alarm or indicator, or automatically by a controller and associated control processor.

As a consequence of the direct delivery of bipolar RF energy through the bipolar electrode pairs 82, the treatment zones of tissue through which the current flows are transformed into the previously described support structure or bridge, such as a series of annular rings or areas 88 of high density desiccated tissue of reduced volume (HDTR), preferably exhibiting characteristics of generally uniform tissue heating, with no charring, controlled lesion width and maximum lesion tissue depth. The support structure or rings 88, as a result of their increased density and stiffness from the RF energy, resist compression or collapse of the urethral passageway, and help provide an enlarged passageway through the prostate relieving the symptoms of BHP.

As explained earlier, the illustrated electrode pairs are preferably spaced apart sufficiently to allow viable endothelial tissue 90 to remain between each HDTR. It is known from prior use of bipolar ablation, such as in the Isolator™ bipolar clamp for cardiac tissue (made by Atricure, Inc. of Cincinnati, Ohio), that lesions created by bipolar energy retain their structural integrity over time, exhibit minimal inflammation, re-endotheliaze over a period of weeks and do not necrose. In the present treatment of BHP, it is believed that the presence and the assistance of viable rings of tissue 90 located between the HDTRs 88 in the urethra will promote re-endotheliazation over a relatively short time after treatment.

In addition to the advantages of the treatment described above for enlarging the urethral passageway to treat the symptoms of BHP, at the same time, the integrity of the sphincter muscle has been preserved and protected from consequences of the RF energy exposure to the prostate. Following completion of the procedure, the retention and treatment members or balloons can be retracted or deflated, and the catheter withdrawn into the sheath, and the sheath and catheter can be removed from urethra.

Turning now to a more detailed description of the illustrated treatment balloon and the associated electrodes, as previously discussed, the treatment balloon(s) 78 can be formed with any suitable material with such degree of compliance as may be desirable for treatment of BHP. Preferably, the illustrated balloon may be formed of relatively non-compliant material such as polyethylene terapthalate (PET) such that the balloon expands to a selected diameter and then does not expand substantially further even though inflation pressure may be increased. The retention and treatment balloons 76, 78 may be attached to the catheter shaft 74 in accordance with well known techniques, such as those well known in the fabrication of urinary, cardiac and other types of catheters.

One non-exclusive example of how the electrodes 80 may be mounted on a treatment balloon is shown in FIGS. 15-20. To aid in mounting the electrodes 80 on the illustrated treatment balloon 78, and to provide conduit runs for electrical communication with each of the electrodes, a slightly raised member or rib 92 extends longitudinally along the surface of the balloon between at least the proximal and distal end portions of the balloon. The rib 98 may be made of any suitable material, but preferably has sufficient flexible or elastic properties to allow expansion and contraction with the balloon itself. In the illustrated embodiment the balloon has a pair of such ribs, mounted approximately 180° apart on opposite sides of the balloon. More or fewer such ribs may be employed, as desired, to assist in maintaining the electrodes in the desired position along the longitudinal axis of the balloon and to provide electrical communication between the electrodes and a generator/sensing unit.

As may be easier seen in FIGS. 15, 17, 20-22 the ribs have transverse slots 94 spaced along the ribs at the desired longitudinal location of the electrodes 80. The electrodes extend around the treatment balloon and through the slots, which serve at least two purposes. First, the slots retain the electrodes in the proper longitudinal position along the balloon, so that the HDTRs are formed in the desired locations. In addition, the slots provide a connection location for connection of the electrode to the conductive leads that extend from the electrodes to the proximal end of the catheter for connection to the generator/sensing unit. FIG. 17 is a cross-sectional view of a portion of the balloon 78 wall, and rib 92, taken along line D-D of FIG. 16. As can be seen there, each raised rib provides a longitudinal conduit run 96 on the underside of the rib, between the rib and surface of the balloon, for dedicated leads 98 that extend between the electrodes and proximal end of catheter. Of course, the conduit channel may be located within an enclosed lumen within the rib or, along the exterior surface of the rib or in some other manner suitable for communicating between a RF generator and sensing unit and the electrodes 80. As illustrated, each rib provides a conduit run for 6 conductive leads (wires) 98, and two ribs accommodate a total of 12 electrodes or 6 electrode pairs on the treatment balloon. Of course, other techniques or structures may be used to retain the electrodes in the desired position at their desired location spaced along the balloon, such as clips, hooks, adhesive or other retention means.

Each lead is preferably insulated from other leads and electrical connection between each lead 98 and its respective electrode 80 may be made in any suitable manner. As illustrated, electrical connection between each lead 98 and its respective electrode 80 is provided in one of the slots through which the respective electrode extends, as illustrated in FIGS. 18 and 22. FIG. 18 is a transverse cross-sectional view through a rib and the balloon wall at one of the slots 94. As seen there and in FIG. 22, which is a longitudinal sectional view, the distal end of the lead 98 extends radially outwardly from the conduit run 96 and connects to its respective electrode 80 that extends through such slot.

In the illustrated embodiment, the desiccators/energy emitters electrodes are illustrated as being extensible, such as of an stretchable coil configuration to accommodate balloon expansion and contraction. More specifically, each electrode ring comprises a generally continuous conductive material such as stainless steel, nitinol or other shape memory metal, copper or other material that can be formed into a coil configuration to allow for expansion and contraction with inflation and deflation of balloon. As described earlier, the electrodes may also have any suitable coating or plating that serves to enhance energy transfer to the tissue of the phosphate and/or a bladder neck. In addition, the electrodes may be coated or plated with material that retard or reduce adhesion between the electrode and the tissue that does not substantially interfere with conducting current between electrodes of adjacent pairs between electrodes within each pair. The illustrated electrodes may specifically be made of silver plated copper.

As pointed out above, treatment times, energy used, and HDTR formation will depend on a number of variables, the details of which can be varied without departing from this disclosure. The following is exemplary of one design configuration for the treating balloon and associated electrodes and treatment conditions. FIG. 20 is an enlarged side view illustrating two electrode pairs 82-2 and 82-3, from the embodiment of FIGS. 15-19 and 21-22, in contact with prostate tissue 26 during treatment. The dimensions shown are for purposes of illustration only and any suitable dimensions or range of dimensions may be selected for the desired treatment. More specifically, however, the illustrated dimensions are as follows: We is the width of each electrode 80 and is in the range of about 1-5 mm and nominally about 1 mm. Se is the spacing between the electrodes 80 within each pair 82 and, as illustrated, the spacing may be in the range of about 1-5 mm and nominally is about 2 mm. Smaller size electrodes may require a closer spacing between the electrodes of each electrode pair and may require a closer spacing between adjacent electrode pairs so as to form the desired supporting structure within the prostate. Conversely, larger dimensional electrodes may allow for larger spacing and fewer electrode pairs spaced along the length of the treatment balloon.

Whether the electrodes are larger or smaller, it is presently deemed desirable to retain spacing between the desiccation zones or locations, such as between the electrode series or pair, that allows a region or ring of viable tissue to be maintained adjacent to the desiccated areas to promote re-endotheliazation, however this may not be necessary. Sr is the spacing between adjacent series or pairs of electrodes. More specifically, Sr, as illustrated, is the distance between the midpoint between electrodes of one electrode group, series or pair and the midpoint between electrodes of an adjacent electrode group, series or pair. Sr is, for purposes of illustration, about 1-2 cm, with a nominal distance of about 1 cm for the electrodes identified above.

When the electrodes of each pair are connected to opposite poles of a bipolar RF energy source, current flows between the electrodes through the contacting tissue. This current heats the tissue, and as explained earlier is understood to desiccate the tissue, cross linking the proteins within the tissue, shrinking the tissue and increasing its density—in essence, forming a relatively stiff biological ring or hoop within the prostate or bladder neck tissue which resists compression and resists reclosure of the urethra. For purposes of illustration, the zone of treated tissue or HDTR is illustrated as a hemispherical section of tissue that is cross hatched in FIGS. 15, 19 and 20. For the electrode arrangement described above, as illustrated in FIG. 20, the zone or area of such desiccated tissue may for example have a depth D1 ranging from about 4-10 mm, with a nominal depth of about 7 mm and a width W1 about 6-8 mm with a nominal width of about 8 mm, and spaced about 1 cm apart. Of course, these dimensions will vary depending upon the electrode configuration, the current flow between the electrodes of each pair, the time of treatment and the energy applied to the tissue. However, test results indicate that in general, over a wide range of energy voltage and current the maximum lesion depth generally corresponds to the lesion width.

$W_t$ represents the width of viable, undesiccated tissue between the high density tissue rings or HDTRs so as to promote the re-growth of a healthy inner endothelial layer of urethral tissue over the high density rings. As illustrated it may be about 2 mm, or more or less as desired. Although it is not understood that such intermediate viable tissue is absolutely required for proper functioning of the device or the resulting enlargement or the resulting treatment of BHP or re-endotheliazation, it is believed to be potentially beneficial for faster re-endotheliazation of the urethra.

For the electrode arrangement described above, it is understood that the entire time for bipolar energy delivery is preferrably less than about 5 minutes, and the total energy delivered may be from about 2000 to about 5000 joules per electrode series or pair and more specifically approximately 15,000 joules for the six electrode pairs shown (about an order of magnitude less energy than the energy applied in other BHP treatments). More specifically, and as non-limiting examples, a 500 kHz bipolar generator/sensing unit may be employed having the ability to set voltage "Ve" and current "Ie" limits up to about 75V and 1400 ma. In preliminary testing the bipolar voltage limit between electrodes of adjacent pairs was about 15 to 25 volts, with a current limit of about 300-500 ma and an energy delivery time ("Te") of about 1-3 minutes. More specifically, based on preliminary testing and practical considerations that favor the smaller electrodes and electrode spacing, the following were identified for potential evaluation: We of about 1 mm and Se of about 2 mm, Ve of about 15+/−3 Volts, Ie of 400+/−50 mA, Te of 3+/−0.5 min and about 15 watts of RF energy. Other electrodes, electrode spacing and arrangements or configuration may require different treatment energies and times.

Although the energy emitters/desiccators/electrodes shown above are expandable coil electrodes, other expandable electrodes may also be used. FIGS. 23A and 23B show another possible expandable electrode pair configuration, employing coiled wires 100 that wrap around the balloon multiple times, as illustrated in FIG. 23A, when in the smaller pre-deployed configuration, and expand to form a continuous electrode of significantly larger diameter when the balloon is expanded, as represented in FIG. 23B.

FIGS. 24A and 24B show yet a further possible embodiment for a pair of electrodes 102. There, the electrodes are arranged in parallel spiral configuration. The illustrated electrodes are spaced uniformly apart by a web 104. More specifically, the electrodes may be wires that are overmolded by plastic material that forms the web and coats the wires to form an integral electrode pair structure that may be affixed to the surface of a treatment balloon. FIG. 24 shows that the configuration may have a small or reduced diameter, such as during insertion into the urethra, and a larger diameter expanded condition upon treatment balloon expansion.

FIGS. 25A and 25B show a further possible embodiment of energy emitters or desiccators in which electrodes 106 are part of a preformed structure, generally at 108, that provides a plurality of electrode ring pairs 110 and associated electrical leads or connectors 112, for mounting on or use with a treatment balloon or other expandable structure. Each ring pair has the electrodes of each pair pre-arranged in the desired spacing Se for bipolar RF energy treatment, and the electrode pairs are spaced apart with a pre-determined distance Sr between them to leave viable tissue regions between adjacent electrode pairs—for the purposes described above. Although the electrodes may not provide a continuous circle of high density tissue in the prostate because of gap 114 that permits expansion of the electrodes, it is believed that such gap will not unduly detract from the resistance of the treated tissue against reclosure of the urethra. Also, any such gap can be bridged by rotation of the electrodes within the prostate until the electrodes bridge the gap and then the electrodes can be energized a second time or third time as necessary to provide complete rings of high density tissue (HDTR) in the prostate and, if desired, the bladder neck.

FIGS. 26-32 show apparatus, system and procedure similar to that described above with respect to FIGS. 9-22, except that the sheath is of different construction. As shown in FIGS. 26 and 27, sheath 116 has only a single pair 118 of electrodes 120 at the distal end thereof, connected via electrical leads (not shown) that extend through the sheath. The sheath may include, as with the prior sheath 66, a plurality of depth or position markings 122 on the exterior surface visible to the user to aid in gauging extent of insertion of the sheath into the urethra.

The procedure employing the sheath 116 is similar to that using sheath 66, except that the tissue profiling is achieved by moving the sheath through the urethra and gauging the impedance or other electrical characteristic of the tissue either continuously or at specific intervals during advancement and/or retraction of the sheath. The insertion step shown in FIG. 28 is otherwise like that described above, with the sheath 116 extended all the way into the bladder neck 24. FIG. 9 illustrates gradual withdrawal or pullback of the sheath 116, during which impedance or other electrical characteristics of the tissue may determined for the first time or, optionally, used to verify the tissue characteristics sensed during insertion.

FIG. 30 shows the sheath 116 inserted to the bladder neck 24 and a treatment device in the form of catheter 72, essentially identical to that described earlier, inserted through the sheath, whereby the sheath and catheter form a treatment system that is particularly advantageous. FIG. 31 shows the retention balloon 76 inflated and FIG. 32 shows the sheath 116 withdrawn to a position within and protecting the urethral sphincter 28. The remaining steps of the procedure upon expansion of the treatment balloon 78 and energizing of the electrodes 80 are the same as described earlier.

Although the figures above show an expandable structure in the form of a balloon, as previously described, the expandable member is not necessarily a balloon or balloons, and FIGS. 33-36 illustrate one form of a non-balloon expandable structure. FIG. 33 shows a sheath or introducer cannula 122 inserted through the urethra 22 into the bladder neck 24. FIG. 34 shows the distal end of sheath 28 withdrawn into the sphincter 28 and an expandable cage, basket or open wire structure 124 residing in collapsed or compressed condition within the prostate 26.

FIGS. 35 and 36 show the cage or structure 124 in an expanded condition with the prostate removed for clarity. As shown there, the structure includes a plurality of longitudinal wires 126, joined at proximal and distal ends 128 and 130 and having a weakened central joint or preferential bend area 132. When the compressive force holding the structure in the position shown in FIG. 34 is released or when proximal tension is applied to the distal joint 130, the wires bend outwardly at the preferential bend area, expanding the diameter of the structure and the urethra within the prostate.

For creating a supporting structure of high density cross-linked tissue within the prostate, point energy emitters/receivers in the form of electrodes 134 are located at spaced locations along the wires of a non-balloon expandable structure. Such non-balloon structure could also use ring-shaped electrodes or electrodes of other configuration. Although different arrangements may be used, it is contemplated that the electrodes at a given longitudinal position would have alternating bipolar polarities from one wire to the next. For example, electrode 134-1 would have opposite polarity to electrode 134-2 and electrode 134-3 would have polarity opposite to 134-2, and so forth, around the wires. As a result, current flow between the electrodes on adjacent wires would create a ring or ring-like line of high density tissue in the urethra and prostate. The plurality of electrodes along the wire would therefore create a plurality of HDTRs spaced apart approximately a distance Sr along the prostate.

Various alternative structures and methods not identical to those described above for purposes of illustration may be employed, as one of ordinary skill would understand, while making use of the concepts disclosed and claimed herein.

What is claimed is:

1. Apparatus for remodeling a tissue lumen comprising:
   an elongated shaft having proximal and distal end portions;
   at least one expandable structure located at the distal end portion and being movable between a retracted position for insertion into and withdrawal from the lumen and an expanded position for enlarging a selected portion of the lumen;
   at least one tissue desiccator carried on the expandable structure in a preselected configuration for contacting lumen tissue when the expandable structure is expanded;
   the preselected configuration being operable for defining in the lumen tissue a support structure of desiccated tissue that resists closure of the lumen; and
   an elongated hollow sheath having a lumen for slidably receiving the elongated shaft and at least one sensing station on the sheath for contacting lumen tissue and sensing an electrical characteristic of tissue therearound prior to desiccation, the sheath being relatively movable along and over the shaft to shield at least one dessicator from lumen tissue,
   the at least one tissue desiccator comprising a plurality of electrode pairs at spaced apart locations on the expandable structure, each pair comprising two spaced electrode rings configured to contact tissue upon expansion of the expandable structure, the electrodes of each pair being connectable to opposite poles of an rf generator to form, when energized, an annular ring or hoop of desiccated tissue in the lumen, whereby a plurality of spaced apart annular desiccation tissue rings may be formed in the lumen to support it in an open condition.

2. The apparatus of claim 1 in which the expandable structure includes at least one balloon, basket, cage or open framework.

3. The apparatus of claim 1 in which the expandable structure has a plurality of regions that expand to different cross-sectional sizes.

4. The apparatus of claim 3 wherein the expandable structure includes at least a proximal region, a distal region and an intermediate region therebetween, and when expanded, the intermediate region has a larger cross-sectional size than the proximal and distal regions.

5. The apparatus of claim 1 wherein the expandable structure comprises an inflatable balloon that has a proximal end portion, a distal end portion and an intermediate portion;
   the balloon having a length sufficient to extend through a male urinary tract substantially between the urinary sphincter and bladder neck such that the proximal portion is located in the vicinity of the sphincter and the distal portion is located in the vicinity of the bladder neck and the intermediate portion is located within the prostate gland, the intermediate portion of the balloon when expanded having a cross-sectional size sufficiently large to enlarge the cross-sectional size of the urethra and the proximal and distal portions having a smaller expanded cross-sectional size than the intermediate portion.

6. The apparatus of claim 1 further including a monitor that senses before desiccation the electrical characteristic of lumen tissue surrounding at least one of the desiccators.

7. The apparatus of claim 6 wherein the monitor generates information based at least in part on the electrical characteristic sensed for determining different types of tissue surrounding the desiccator.

8. The apparatus of claim 1 further comprising a plurality of sensing stations disposed along the sheath.

9. The apparatus of claim 1, the sheath including a plurality of sensing stations spaced apart along the sheath, the sensing stations being respectively spaced apart substantially the same distance that the dessicator pairs are spaced apart.

10. A method for remodeling a tissue lumen comprising:
advancing an elongated hollow sheath into the tissue lumen, the sheath including a lumen and at least one sensing station on the sheath for contacting lumen tissue before desiccation,
advancing an elongated shaft through the lumen of the sheath, the shaft including at least one expandable structure located at a distal end structure of the shaft, the expandable structure being movable between a retracted position for movement through the sheath or tissue lumen and an expanded position for enlarging a selected portion of the lumen, and at least one tissue desiccator carried on the expandable structure in a preselected configuration for contacting lumen tissue when the expandable structure is expanded, the preselected configuration defining a tissue support structure in the lumen tissue that resists closure of the lumen;
sensing an electrical characteristic of lumen tissue with the sheath sensing station before desiccation, identifying prostate tissue based on the sensed electrical characteristic and relatively positioning the sheath and shaft to shield lumen tissue from a portion of the shaft;
enlarging a selected length of the tissue lumen by expanding the expandable structure; and
desiccating tissue of and surrounding the tissue lumen with the at least one desiccator while the expandable structure is enlarged, in a predetermined pattern that resists closure of the tissue lumen.

11. The method of claim 10 including distinguishing prostate tissue from urinary sphincter tissue or bladder neck tissue based on sensed electrical characteristic before desiccation.

12. A method for remodeling a tissue lumen of a human urinary tract comprising:
advancing an elongated hollow sheath into the tissue lumen, the sheath including a lumen and at least one sensing station on the sheath,
advancing an elongated shaft through the lumen of the sheath, the shaft including at least one expandable structure located at a distal end structure of the shaft, the expandable structure being movable between a retracted position for movement through the sheath or tissue lumen and an expanded position for enlarging a selected portion of the lumen, and at least one tissue desiccator carried on the expandable structure in a preselected configuration for contacting lumen tissue when the expandable structure is expanded, the preselected configuration defining a tissue support structure in the lumen tissue that resists closure of the lumen;
sensing an electrical characteristic of lumen tissue with the sheath sensing station at spaced locations along the urinary tract before desiccation, creating a profile of the sensed electrical characteristic of tissue along the tissue lumen before desiccation; and relatively positioning the sheath and shaft to shield lumen tissue from a portion of the shaft;
enlarging a selected length of the tissue lumen by expanding the expandable structure; and
desiccating tissue of and surrounding the tissue lumen with the at least one desiccator while the expandable structure is enlarged, in a predetermined pattern that resists closure of the tissue lumen.

13. The method of claim 12 in which the profile is generated before the enlarging step.

14. The method of claim 12 including distinguishing prostate tissue from urinary sphincter tissue or bladder neck tissue based on sensed electrical characteristic before desiccation.

15. Apparatus for remodeling a tissue lumen comprising:
an elongated shaft having proximal and distal end portions;
a plurality of tissue desiccators spaced apart along the shaft;
at least one expandable structure located at the distal end portion and being movable between a retracted position for insertion into and withdrawal from the lumen and an expanded position for enlarging a selected portion of the lumen;
at least one tissue desiccator carried on the expandable structure in a preselected configuration for contacting lumen tissue when the expandable structure is expanded;
the preselected configuration being operable to defining in the lumen tissue a support structure of desiccated tissue that resists closure of the lumen and;
an elongated hollow sheath having a lumen for slidably receiving the elongated shaft and a plurality of sensing stations spaced apart along the sheath for contacting lumen tissue and sensing an electrical characteristic of tissue therearound prior to desiccation, the sensing stations being respectively spaced apart substantially the same distance that the tissue desiccators are spaced apart, the sheath being relatively movable along and over shaft to shield at least one desiccator from lumen tissue.

16. The apparatus of claim 15 further comprising a monitor that monitors the electrical characteristic of tissue surrounding each of the sensing stations.

17. The apparatus of claim 16 wherein the monitor provides user information to distinguish tissue types based at least in part on the sensed electrical characteristic.

* * * * *